(12) United States Patent
Hames et al.

(10) Patent No.: US 9,633,175 B2
(45) Date of Patent: Apr. 25, 2017

(54) INTERACTIVE SYSTEM FOR SLEEP IMPROVEMENT

(71) Applicant: Big Health Ltd.

(72) Inventors: Peter Hames, London (GB); Colin Espie, Kilmacolm Inverclyde (GB)

(73) Assignee: BIG HEALTH LTD, London (GB)

( * ) Notice: Subject to any disclaimer, the term of this patent is extended or adjusted under 35 U.S.C. 154(b) by 428 days.

(21) Appl. No.: 14/172,347

(22) Filed: Feb. 4, 2014

(65) Prior Publication Data

US 2014/0222720 A1      Aug. 7, 2014

Related U.S. Application Data

(60) Provisional application No. 61/760,955, filed on Feb. 5, 2013.

(51) Int. Cl.
*A61M 21/00* (2006.01)
*G06F 19/00* (2011.01)

(52) U.S. Cl.
CPC ........ *G06F 19/363* (2013.01); *G06F 19/3481* (2013.01)

(58) Field of Classification Search
CPC ................ A61M 21/00; A61M 2021/0005
USPC ..................................... 600/26–28
See application file for complete search history.

(56) References Cited

U.S. PATENT DOCUMENTS

| | | |
|---|---|---|
| 7,654,948 B2 | 2/2010 | Kaplan et al. |
| 8,083,675 B2 | 12/2011 | Robinson et al. |
| 2003/0059750 A1 | 3/2003 | Bindler et al. |
| 2011/0015495 A1 | 1/2011 | Dothie et al. |

FOREIGN PATENT DOCUMENTS

| | | |
|---|---|---|
| JP | 2007-319638 | 12/2007 |
| KR | 100831602 | 6/2008 |
| WO | WO2010/140117 | 12/2010 |

*Primary Examiner* — John Lacyk
(74) *Attorney, Agent, or Firm* — Welsh Flaxman & Gitler LLC

(57) ABSTRACT

A computer-based sleep improvement system applying system intelligence to up-to-date user-reported data and/or recorded sleep data from a connected tracking device for assisting a user in the proactive improvement of sleep and treatment of insomnia includes a central server maintaining a library of information related to treatment of insomnia. The central server includes a video database of session video material, an audio database of session material, a case file database of information regarding the user and sleep habits of the user, and a plurality of tools assisting the user in treating insomnia. The system includes a session coordinator creating sessions of customized presentations for the user based upon the library of information and a user interface linked to the central server.

12 Claims, 20 Drawing Sheets

Service Architecture

Tools

- Sleep Diary ~24
- To Do list ~28
- Daily Schedule ~30
- Library ~32
- 34 — Thought Checker
- 36 — Planner
- Compare sleep tags ~37
- 39 — Recommended reading
- Sleep report ~41
- 38 — Relaxation audio
- 40 — Stats
- 42 — Reminders
- 44 — Community

Content

- Session 1
- Session 2
- Session 3
- Session 4
- Session 5
- Session 6
- Session 7+
- Library
- Progress Review

Motivational system

FIG. 2

Tools

Sleep Diary — 24 — Records daily sleep pattern and quality rating.

To Do list — 28 — Personalized list of persistent tasks, grows through program.

Daily Schedule — 30 — Daily tasks and reminders in a 'looped' 24 hour schedule.

Library — 32 — Repeat access to instructional session content and expert articles.

Stats — 40 — In depth metrics on the user's data.

Thought Checker — 34 — Framework to facilitate evaluation of thoughts.

Planner — 36 — Framework to facilitate putting the day to rest.

Compare sleep tags — 37 — Allows user to compare sleep on nights associated with any particular 'tag' added in the Sleep Diary with their average sleep.

Recommended reading — 39 — A personalized selection of Library articles and Community discussions.

Sleep report — 41 — A representation of the user's Initial Sleep Test data.

Relaxation audio — 38 — MP3 audio to guide 3 x relaxation techniques.

Reminders — 42 — Email and SMS reminders of daily tasks and motivational messages.

Community — 44 — Knowledge bank and peer support network.

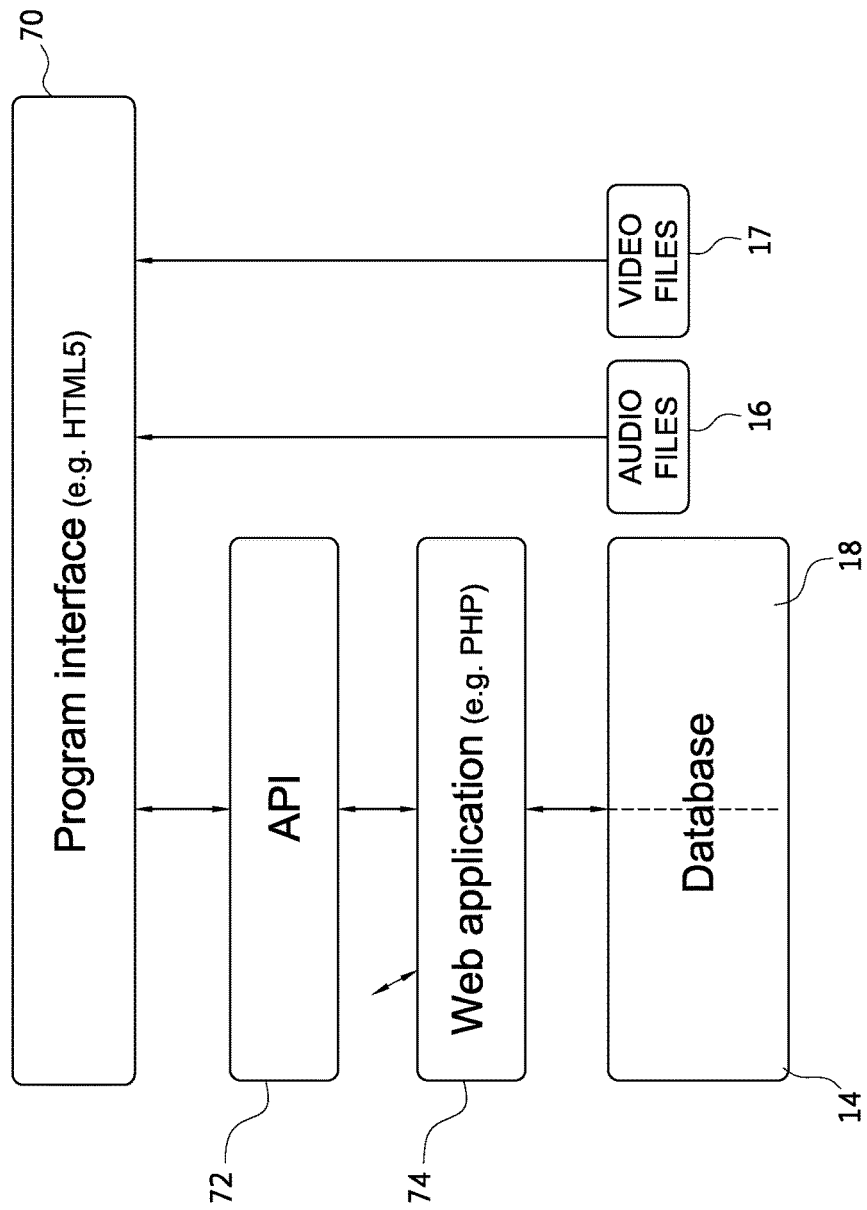

INTERACTIVE SYSTEM FOR SLEEP IMPROVEMENT

CROSS REFERENCE TO RELATED APPLICATION

This application claims the benefit of U.S. Provisional Patent Application Ser. No. 61/760,955, entitled "INTERACTIVE WEB BASED SYSTEM FOR SLEEP IMPROVEMENT," filed Feb. 5, 2013.

BACKGROUND OF THE INVENTION

1. Field of the Invention

The invention relates to a computer system providing assistance in improving the characteristics of user's sleep. More particularly, the invention relates to a computer system working in conjunction with sleep training techniques to assist users and practitioners in the improvement of sleep and treatment of insomnia.

2. Description of the Related Art

Sleep problems confront almost everyone at some point in their life. While many people are able to overcome these problems on their own, others require help. Some of these people requiring help are fortunate to have the assistance of professionals, but many people are forced to deal with their sleep problems without assistance. For those people without external help the likelihood of success is limited and many people are forced to live with their sleep problems for years without being able to remedy the underlying problems.

The present invention provides a computer-based system for those individuals not fortunate enough to have access to a professional capable of helping them improve their sleep habits and overcome their problems with insomnia.

SUMMARY OF THE INVENTION

It is, therefore, an object of the present invention to provide a computer-based sleep improvement system applying system intelligence to up-to-date user-reported data for assisting a user in the proactive improvement of sleep and treatment of insomnia. The system includes a central server maintaining a library of information related to treatment of insomnia. The central server includes a video database of session video material, an audio database of session material, a case file database of information regarding the user and sleep habits of the user, and a plurality of tools assisting the user in treating insomnia. The system includes a session coordinator creating sessions of customized presentations for the user based upon the library of information and a user interface linked to the central server.

It is also an object of the present invention to provide a sleep improvement system wherein each of the sessions is composed of many dynamically-combined individual movie and audio elements appearing to the user as a single seamless interactive movie.

It is another object of the present invention to provide a sleep improvement system wherein the case file database includes data sources employed to personalize the sessions to each user.

It is a further object of the present invention to provide a sleep improvement system wherein the data sources include an initial sleep test, daily sleep diary data, user access patterns, and prompted user input.

It is also an object of the present invention to provide a sleep improvement system wherein the sessions are composed of topics, slides, interactive input sessions and movies/audio.

It is another object of the present invention to provide a sleep improvement system wherein the session coordinator decides upon content for the sessions based on an analysis of the user's initial sleep test information and prompted user input.

It is a further object of the present invention to provide a sleep improvement system wherein the sessions are weekly interactive video-based customized presentation, delivered over the Internet, during which the user learns cognitive and behavioral techniques.

It is also an object of the present invention to provide a sleep improvement system wherein the plurality of tools is progressively unlocked.

It is another object of the present invention to provide a sleep improvement system wherein the plurality of tools are selected from the group consisting of a Sleep Diary, a Library, a Compare Sleep Tags tool, a Relaxation Audio(s), a Sleep report, Reminders and a Community tool.

It is a further object of the present invention to provide a sleep improvement system wherein the user interface is a graphical user interface accessed via a computer connected to a global communication network.

It is also an object of the present invention to provide a sleep improvement system wherein the session coordinator includes functionality for providing email, SMS communications and social networking.

It is another object of the present invention to provide a sleep improvement system wherein the session coordinator includes a program interface, application program interface, and web applications.

It is a further object of the present invention to provide a sleep improvement system wherein the central server is a web-based server allowing for input and retrieval of information.

It is also an object of the present invention to provide a sleep improvement system wherein the plurality of tools includes a Sleep Diary providing a user interface for recording a daily sleep pattern, a quality rating and lifestyle factors.

It is another object of the present invention to provide a sleep improvement system wherein the plurality of tools includes a Compare Sleep Tags tool allowing the user to compare sleep on nights associated with any particular "tag" added in the Sleep Diary.

It is another object of the present invention to provide a sleep improvement system wherein the plurality of tools includes a Library providing a graphical user interface designed to access to instructional content.

It is also an object of the present invention to provide a sleep improvement system wherein the plurality of tools includes a Stats tool providing in-depth metrics on data of the user.

It is another object of the present invention to provide a sleep improvement system wherein the plurality of tools includes a Sleep Report providing a representation of Sleep Test data of the user.

It is another object of the present invention to provide a sleep improvement system wherein the plurality of tools includes a Relaxation Audio providing digital audio designed to allow the user to select MP3 audio to guide relaxation techniques.

It is a further object of the present invention to provide a sleep improvement system wherein the plurality of tools includes a Reminder tool assisting the user in managing and receiving email and SMS reminders of daily tasks and motivational messages.

It is also an object of the present invention to provide a sleep improvement system wherein the plurality of tools includes a Community tool providing a graphical user interface offering the user a peer support network.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 2 is a service architecture overview of the present sleep improvement system.

FIG. 3 is an overview of the various tools employed in accordance with the present sleep improvement system.

FIGS. 4-15 show screenshots of various tools employed in accordance with the present sleep improvement system.

FIG. 20 provides a technical architecture of the central server.

DETAILED DESCRIPTION OF THE INVENTION

Figure 1:
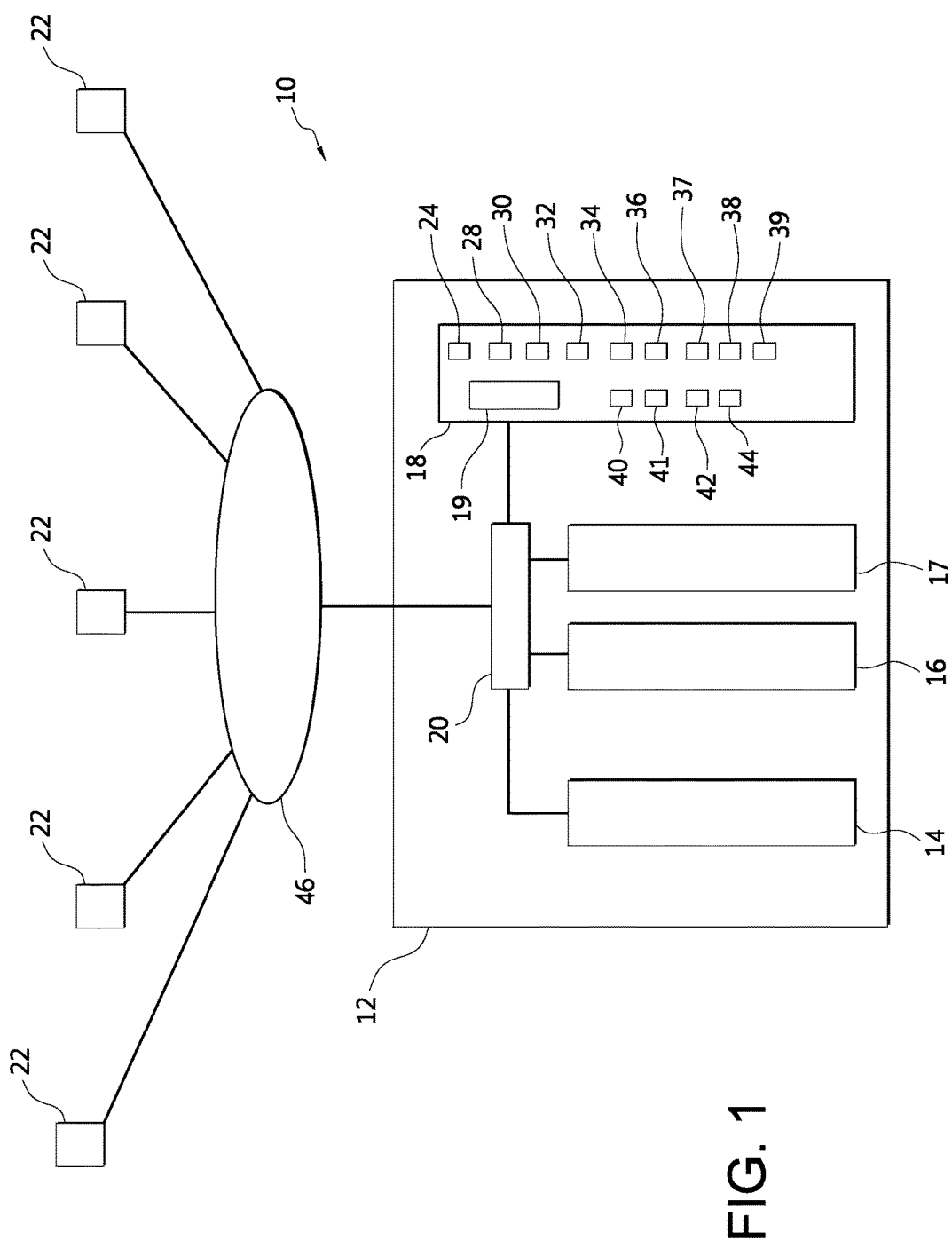
FIG. 1 is a schematic of the present computer-based sleep improvement system.

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for teaching one skilled in the art how to make and/or use the invention.

In accordance with the present invention and with reference to FIGS. 1 to 20, a computer-based sleep improvement system 10 for assisting users and practitioners in the improvement of sleep and treatment of insomnia is provided. The present computer-based sleep improvement system 10 applies system intelligence to up-to-date user-reported data, enabling the sleep improvement system 10 to proactively establish multimedia content personally directed to improving the user's sleeping patterns. The present user driven computer-based sleep improvement system 10 aids the user throughout the entire process, providing online tools which assist the user in both short term and long term improvement in their sleeping characteristics.

The system 10 includes a central server maintaining a library of information related to treatment of insomnia. The central server 12 includes a video database 16 of session video material, an audio database 17 of session material, a case file database 18 of information regarding the user and sleep habits of the user, and a plurality of tools assisting the user in treating insomnia. The system 10 includes a session coordinator 20 creating sessions of customized presentations for the user based upon the library of information and a user interface 22 linked to the central server 12.

Although the present computer-based sleep improvement system 10 is particularly adapted for users focusing on the self-initiated improvement of sleep pattern and quality, access thereto may be provided to practitioners in consideration of the fact much of the treatment for insomnia overflows into other medical specialties and the information available via the present computer-based sleep improvement system 10 would certainly be of interest to a variety of practitioners.

As such, the present invention is a non-transitory software-based sleep improvement system 10 designed to help people improve their sleep. The sleep improvement system is generally composed of a series of weekly or daily interactive video-based 'sessions', delivered over the Internet, during which the user learns cognitive and behavioral techniques to improve their sleep. Each session is presented by 'The Prof', an animated virtual sleep coach. Although each session is composed of many dynamically-combined individual movie and audio elements, it appears to the user as though it is a single seamless interactive movie. The present sleep improvement system makes use of a selection of online tools, progressively unlocked and populated as the user moves through the program, for use by the user to put the techniques they learn into practice between sessions. The present sleep improvement system also includes a library of expert articles on every aspect of the program, unlocked as the user progresses through the program, reminders sent to the user via email and SMS messages, support from an online community of other users, with automated 'matchmaking' of users based on a selection of criteria, and discussion topics unlocked as the program progresses.

The whole program is automated, yet the content and experience is highly dynamic and personalized to each user's particular problems, goals and progress in improving their sleep. As such, every user will have a different experience with the program. The program is designed to maximize their chances of improving their sleep. It is the methods, utilized to personalize the user experience, that constitute the distinctive features of the program implemented in accordance with the present sleep improvement system.

A number of data sources are employed by the system to personalize the pattern and type of content presented to each user: (1) Initial sleep test—At the start of the program the user completes an in-depth questionnaire about their current sleep pattern, lifestyle habits, bedroom environment and nighttime thoughts. This provides a baseline profile of the user and their sleep; (2) Daily Sleep Diary data—Each user is asked to complete a daily record of their sleep throughout the program to track their progress. This is input by the user into an online 'Sleep Diary' form, with a range of multiple choice questions covering their previous night's sleep pattern and quality. This data may be imported from a third party monitoring device or entered manually by the user into the online form via their computer or mobile phone; (3) User access patterns—The system tracks the distance through the program reached by each user, and each time they access any of the online tools; and (4) Prompted user input—During each session the user is asked by the system to make choices and input information to indicate preference and relevance.

Referring to the network diagrams shown in FIGS. 1 and 20, the sleep improvement system 10 includes a central server 12 maintaining a library of information 14 related to the treatment of insomnia, a video database 16 of session video material used in presenting important lessons to the user, an audio database 17 of session material used in presenting important lessons to the user, a Case File database 18 of information regarding specific users and their sleep habits 19 and tools to deal with them and specific interactive tools (that is, computer applications as discussed below in greater detail) 22, 24, 28, 30, 32, 34, 36, 37, 38, 39, 40, 41, 42, 44. As will be explained below in greater detail, all of the data maintained within the central server 12 is utilized by a session coordinator 20, for example, in the form of a microprocessor, to create customized presentations for the users of the present sleep improvement system 10. In addition to providing the processing required for customized presentations, and with reference to FIG. 20, it is further appreciated the session coordinator 20 includes functionality for providing email, SMS communications and social networking. It is accordingly provided with a program interface 70, application program interface 72, and web applications 74 as shown in FIG. 20.

In accordance with a preferred embodiment of the present invention, the central server 12 is a web-based server allowing for the input and retrieval of information in a highly efficient manner. The sleep improvement system 10 further includes a user interface 22 linked to the central server 12. In accordance with a preferred embodiment of the present invention, the user interface 22 is a graphical user interface accessed via a computer connected to a global communication network, for example, the Internet 46, for interaction with the central server 12. The user interface 22 provides for uploading and downloading information to and from the central server 12. The uploaded information is processed by the central server 12 and then made available to the user. The user interface 22 also provides access to information, including, video material, technical literature and interactive user tools stored within the central server 12. The information is selected from a mix of tools from the Case File database 18, the group consisting of a Sleep Diary 24, a To Do List 28, a Daily Schedule 30, a Library 32, a Thought Checker 34, a Planner tool 36, a Compare Sleep Tags tool 37, a Relaxation Audio(s) 38, a Recommended reading tool 39, Stats 40, a Sleep report 41, Reminders 42 and a Community tool 44, as well as other information sources discussed throughout the present disclosure. As will be discussed below in greater detail, the present computer-based sleep improvement system 10 generates data that is available to the user and similarly issues relevant alerts (for example, Email or SMS communications) to the user via the user interface 22 and email or SMS communications.

As those skilled in the art will appreciate, the present sleep improvement system 10 is computer-based and relies upon the protocols of the Internet 46, or other global communication network, to allow for the transfer of information between the user interface 22 and the central server 12 to achieve the purposes and functionalities discussed below in accordance with a preferred embodiment of the present invention. While a preferred mode of implementation is discussed herein, those skilled in the art will appreciate data transfer via various networks is quickly developing and it is contemplated various modes of implementation may be employed without departing from the spirit of the present invention.

In practice and as discussed below, the tools of the computer-based sleep improvement system 10 are ordered and utilized with various training sessions to achieve the desired result of sleep improvement. As discussed above, the tools include a Sleep Diary 24, a To Do List 28, a Daily Schedule 30, a Library 32, a Thought Checker 34, a Planner tool 36, a Compare Sleep Tags tool 37, a Relaxation Audio(s) 38, a Recommended reading tool 39, Stats 40, a Sleep report 41, Reminders 42 and a Community tool 44. For example, and with reference to FIG. 16 during Session One a user might employ two tools, during Session Two a user might employ four tools and during Session Three a user might employ six tools, continuing on until all needed tools are being employed in an effort to achieve the desired result of sleep improvement.

Figure 4:
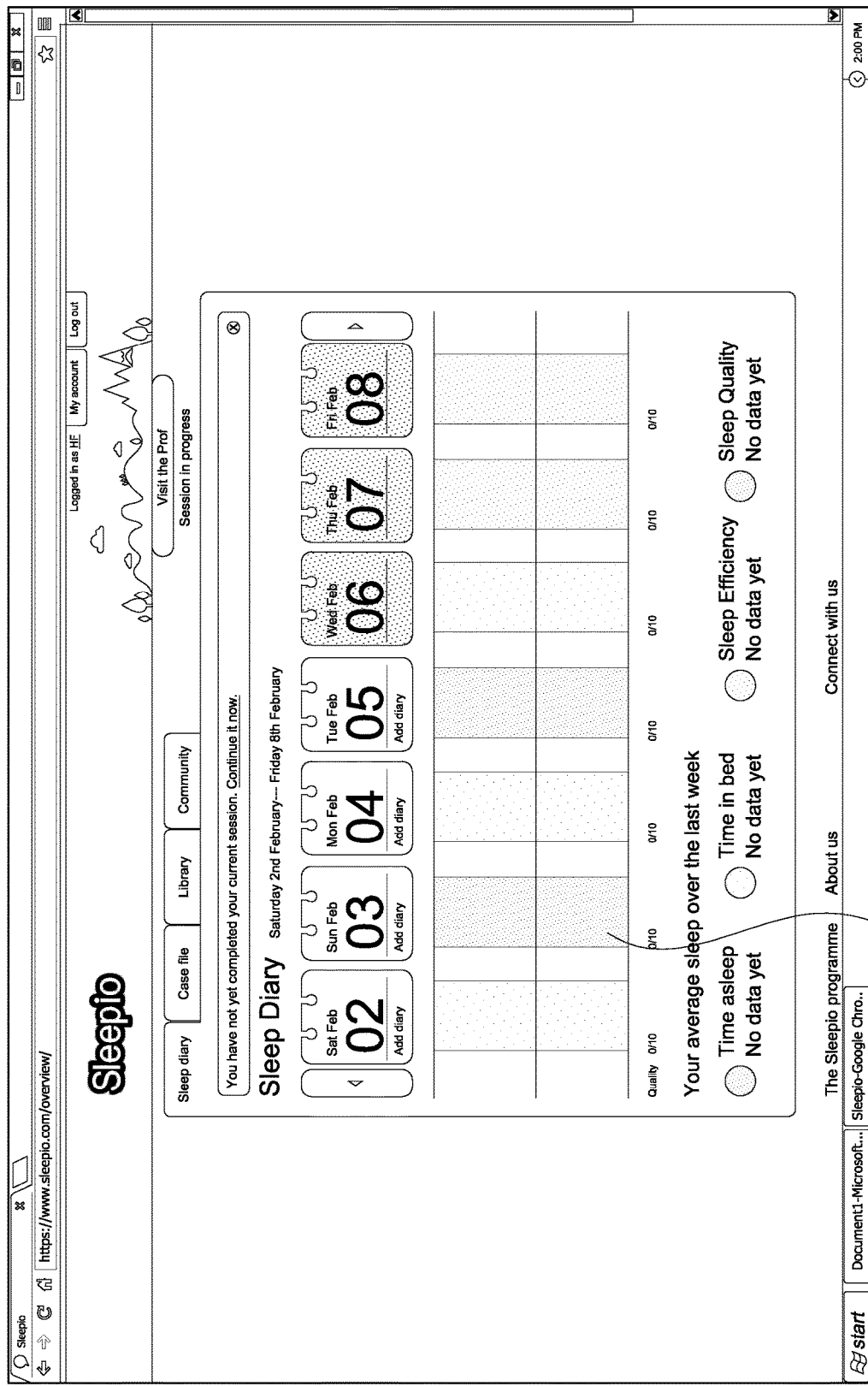
Figure 5:
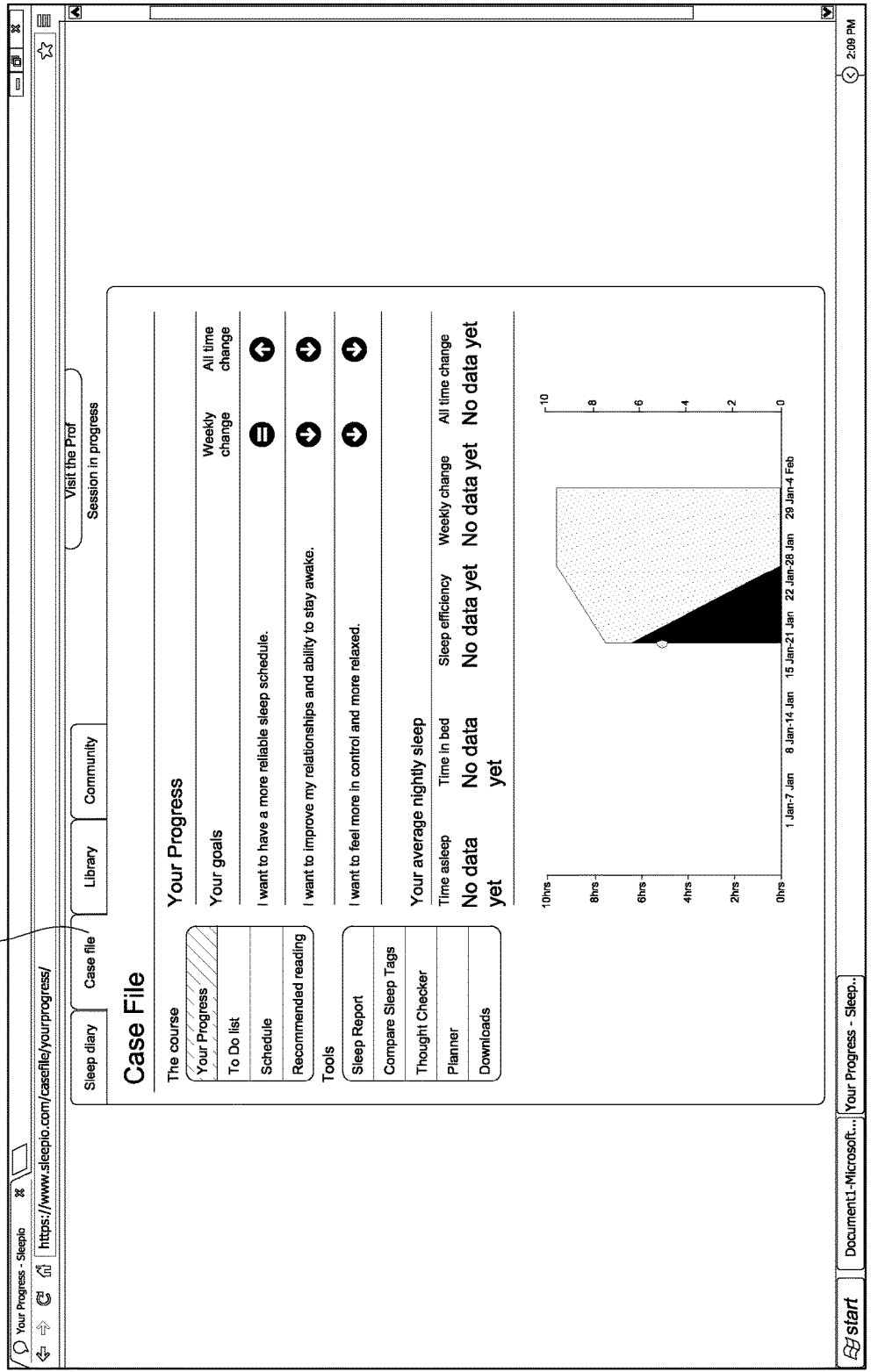

More particularly, each of the tools employs a specific graphic user interface designed for a highly specific purpose. With reference to FIG. 4, the Sleep Diary 24 provides a user interface for recording a daily sleep pattern, a quality rating and lifestyle factors. The Sleep Diary 24 includes various functionalities allowing for ease of input. In particular, the Sleep Diary 24 includes drop down menus for conveniently inputting the time the user gets into bed, the time the user turns out the lights, how long it takes the user to fall asleep after turning out the lights, how often the user wakes up each night, how long it takes the user to get back to sleep after the user wakes up, the time at which the user wakes up and the time at which the user gets out of bed. Finally, an overall rating of the quality of the night's sleep is put into the sleep improvement system 10. The Sleep Diary 24 is updated on a daily basis and the information is stored within the Case File database 18 of the present sleep improvement system 10.

Figure 6:
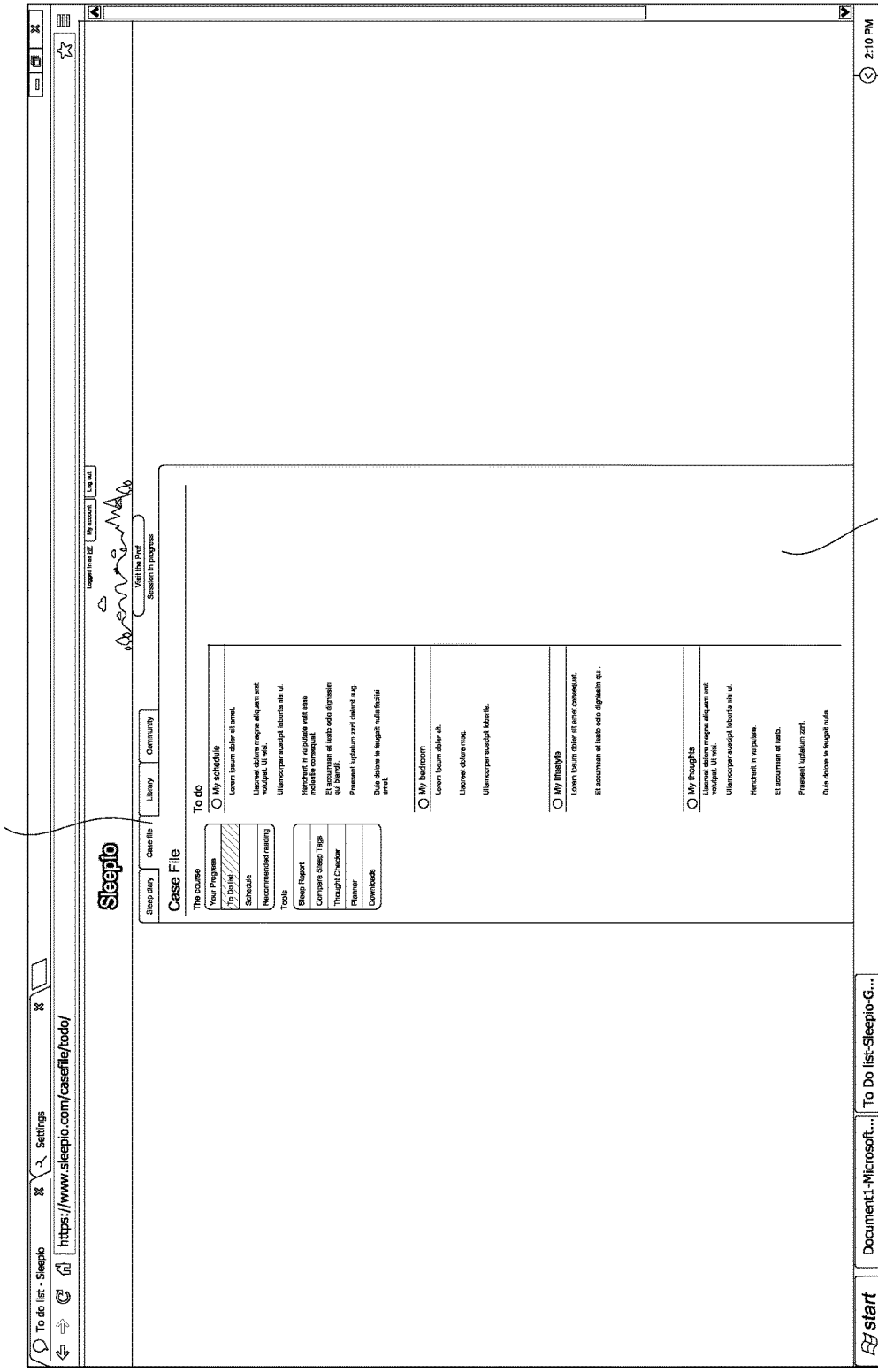
Figure 7:
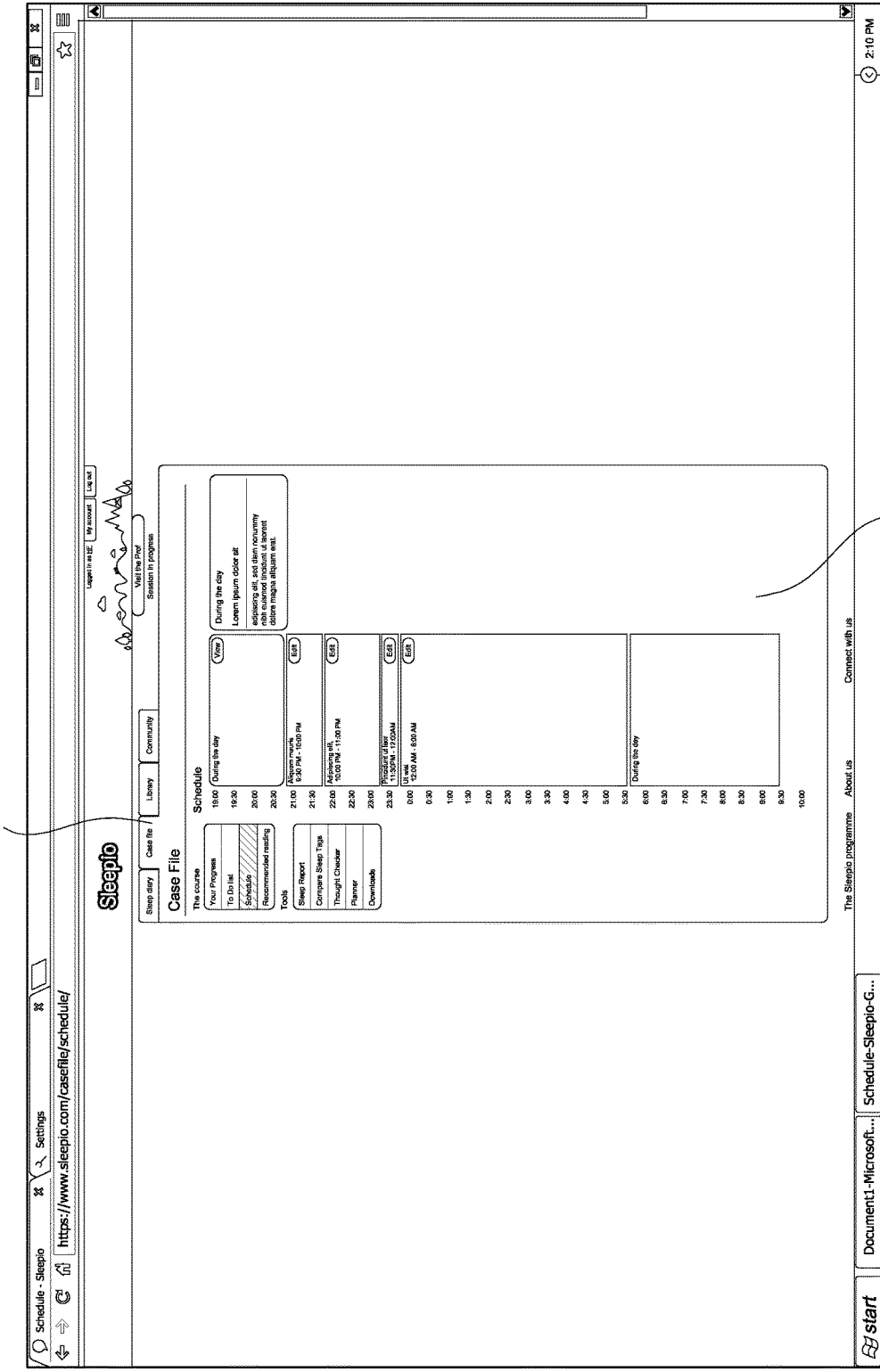
Figure 8:
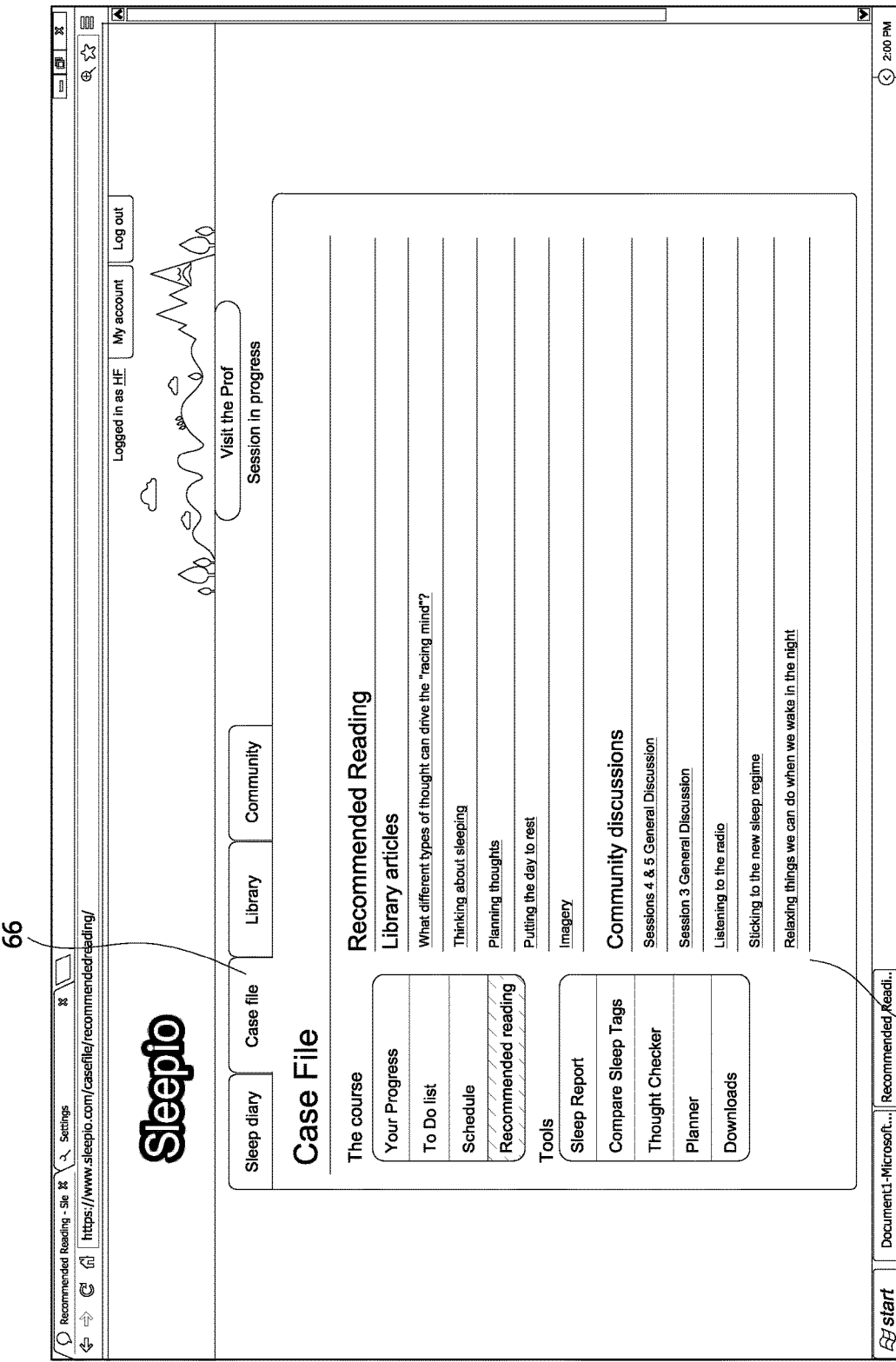
Figure 9:
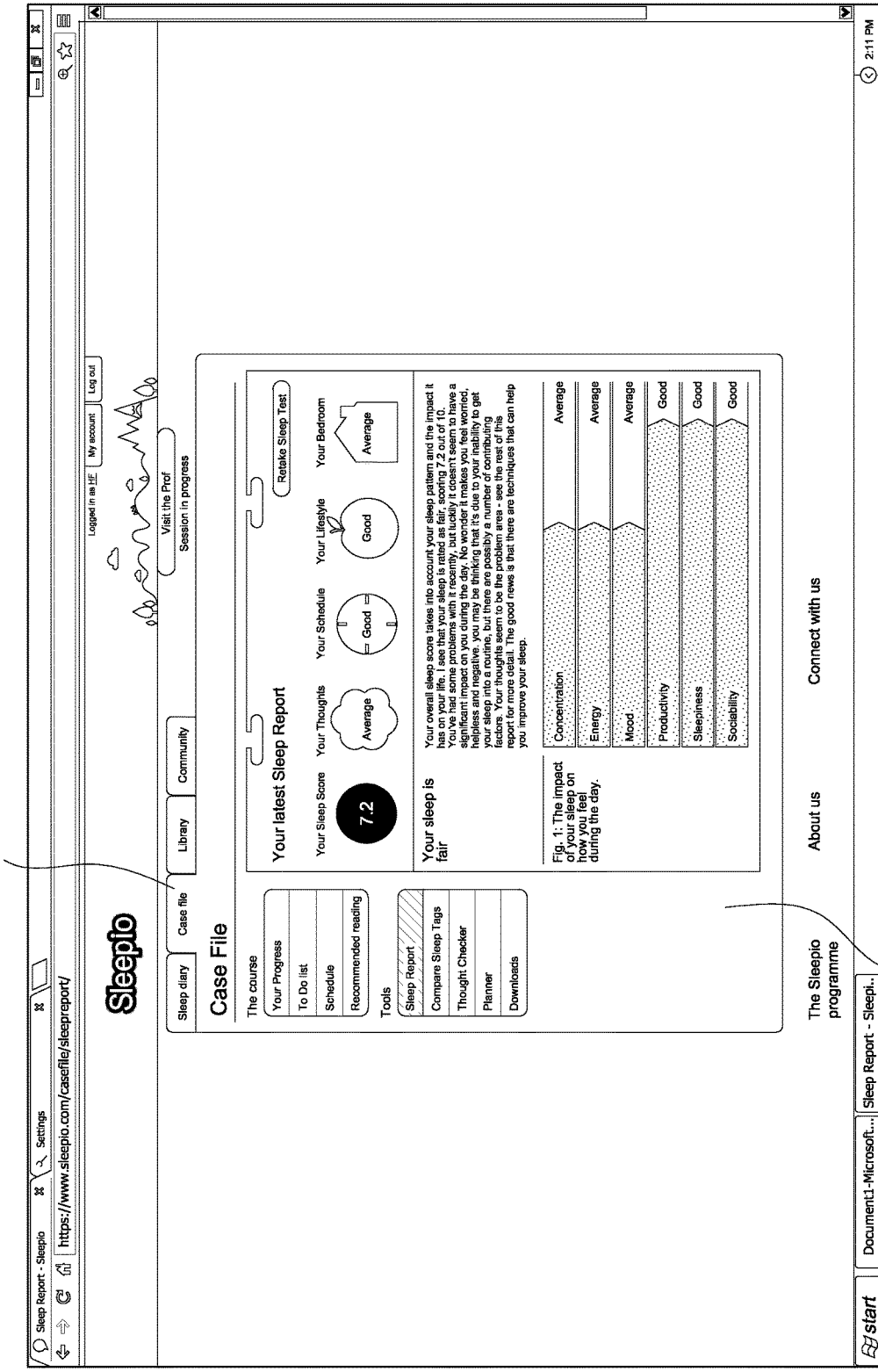
Figure 10:
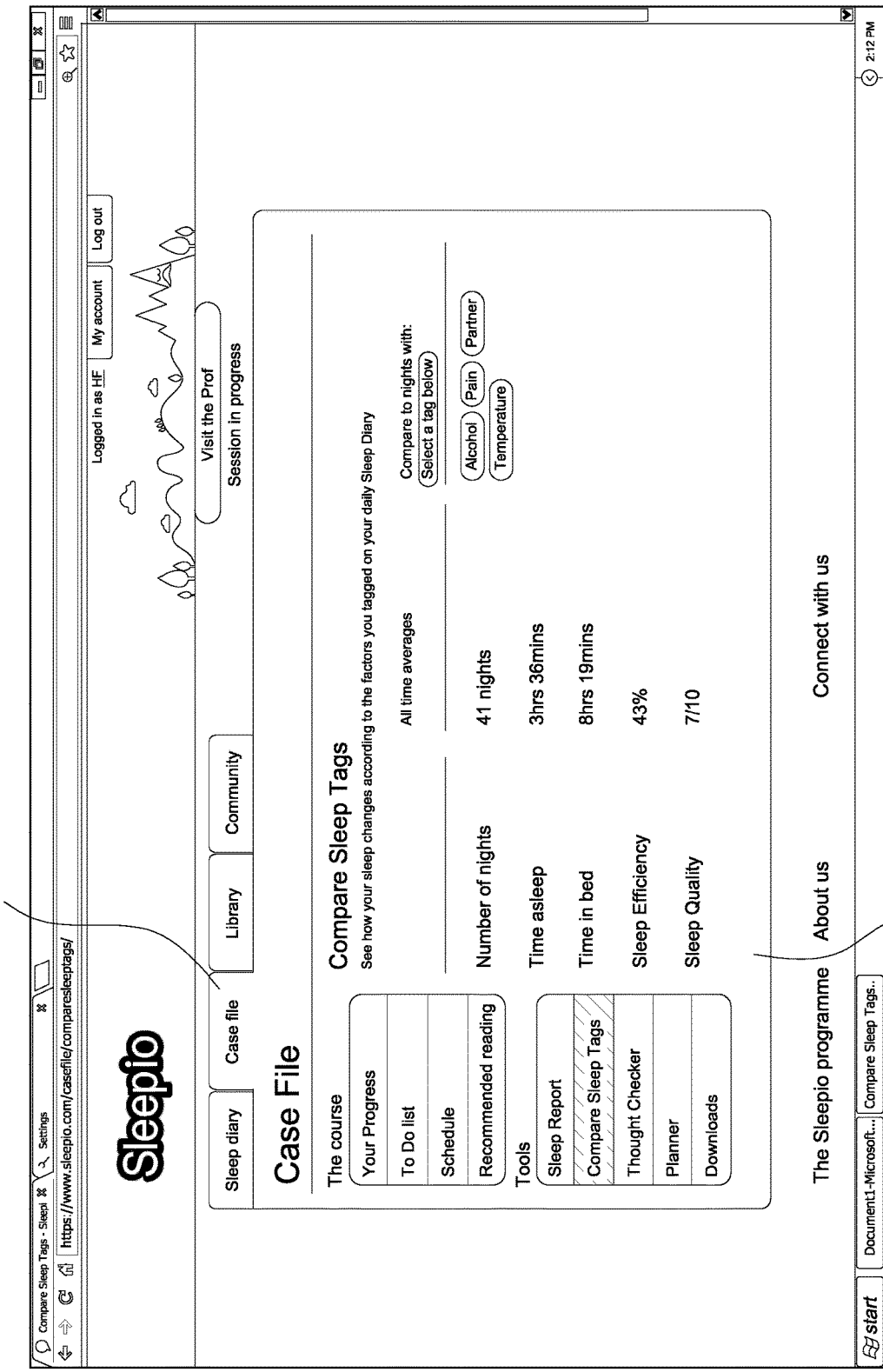

Referring to FIG. 6, The To Do List 28 provides a graphical user interface designed to provide a tailored list of persistent tasks, which grows through the course. The To Do List 28 is organized to focus upon various aspects in the life of the user requiring changes for the purpose of enhancing the user's overall quality of sleep. In accordance with a preferred embodiment, the To Do List 28 includes four sub-lists relating to the user's schedule, bedroom, lifestyle and thoughts. As will be appreciated based upon the following disclosure, the list items are updated using interactive sessions in which the users participate as guided by the present sleep improvement system 10.

The Daily Schedule 30 (FIG. 7) provides a graphical user interface providing the user with daily tasks and reminders in a looped 24 hour schedule.

The Library 32 (FIG. 14) provides a graphical user interface designed to access to instructional content related to the main guidance sessions.

The Compare Sleep Tags tool 37 (FIG. 10) allows the user to compare sleep on nights associated with any particular "tag" added in the Sleep Diary 24.

The Recommended Reading tool (FIG. 8) provides a personalized selection of Library articles and Community discussion.

The Stats tool 40 provides in-depth metrics on the user's data in various reports presented in conjunction with the present invention.

The Sleep Report (FIG. 9) provides a representation of the user's initial Sleep Test data.

Figure 11:
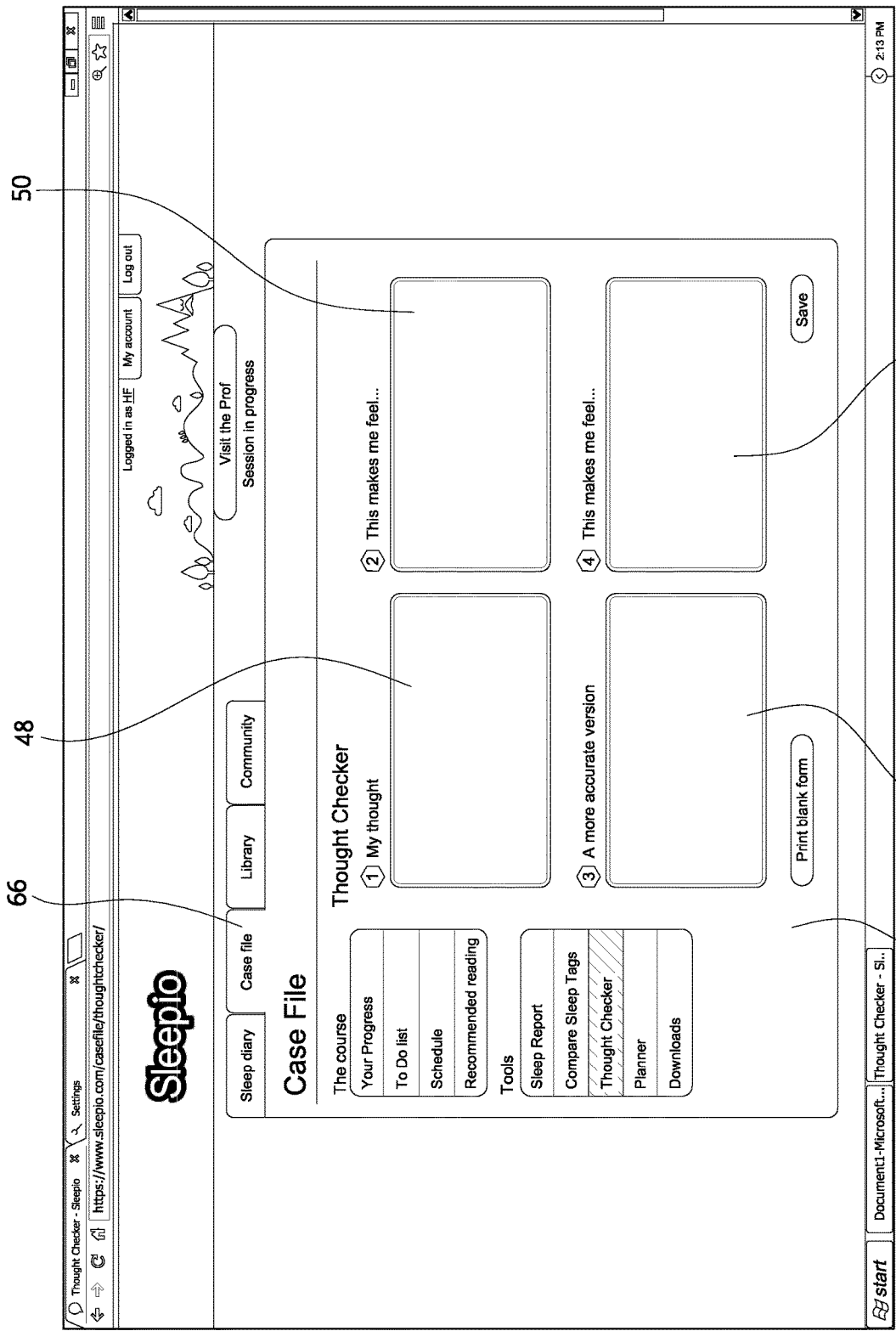
Figure 12:
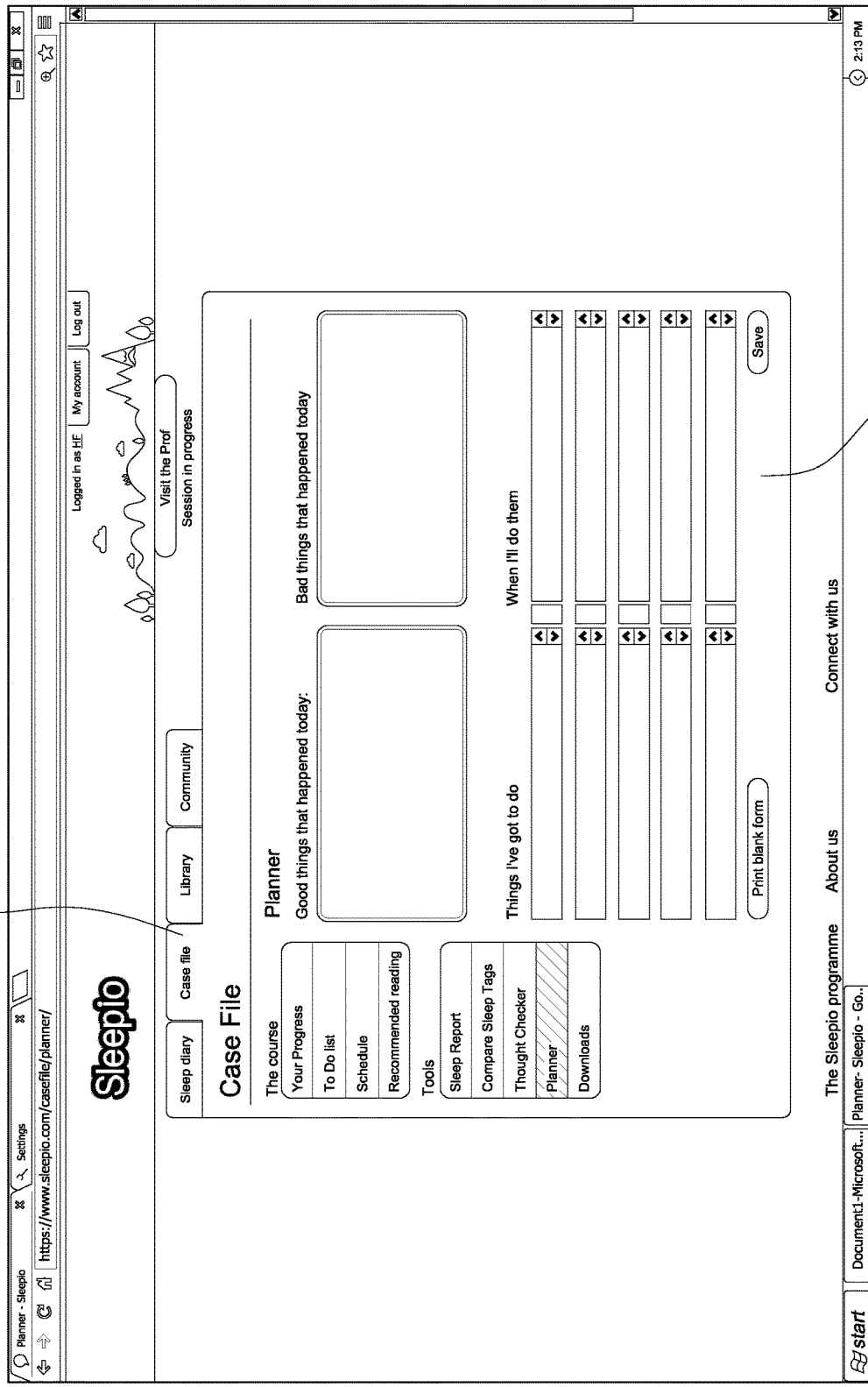
Figure 14:
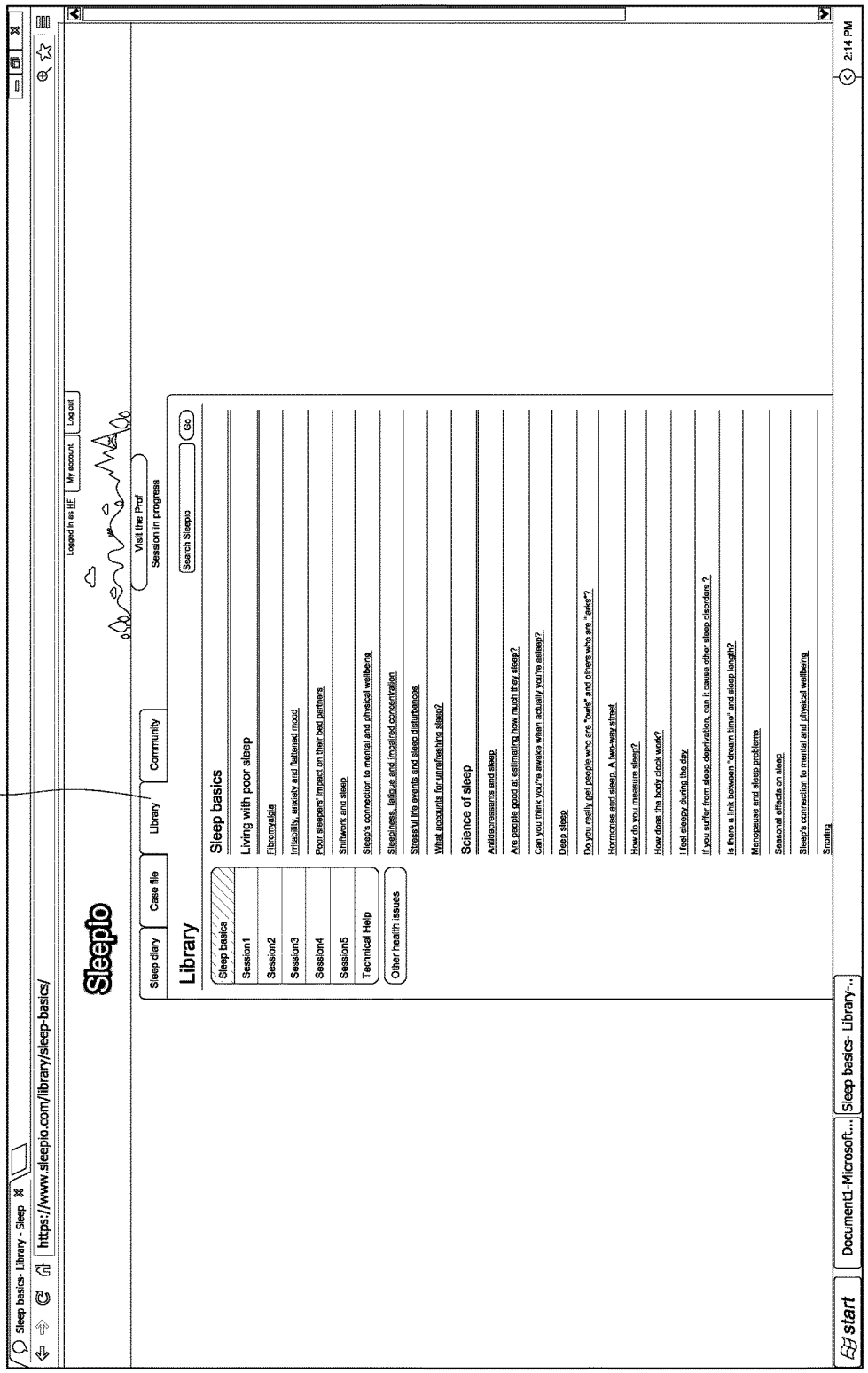
Figure 16:
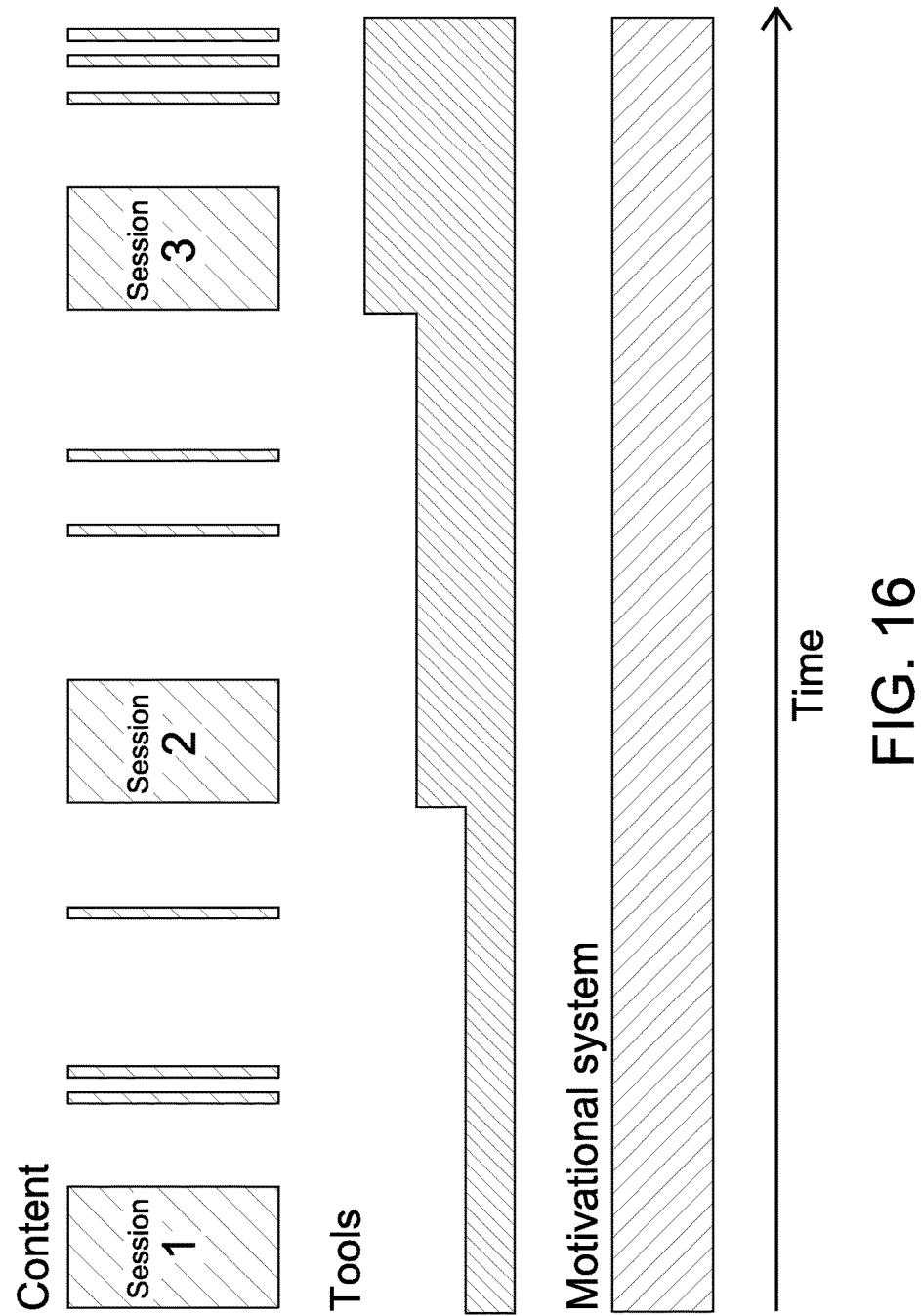
FIGS. 16-19 are schematic of service architecture, content structure, dynamic features, and content types in accordance with the present sleep improvement system.
Figure 17:
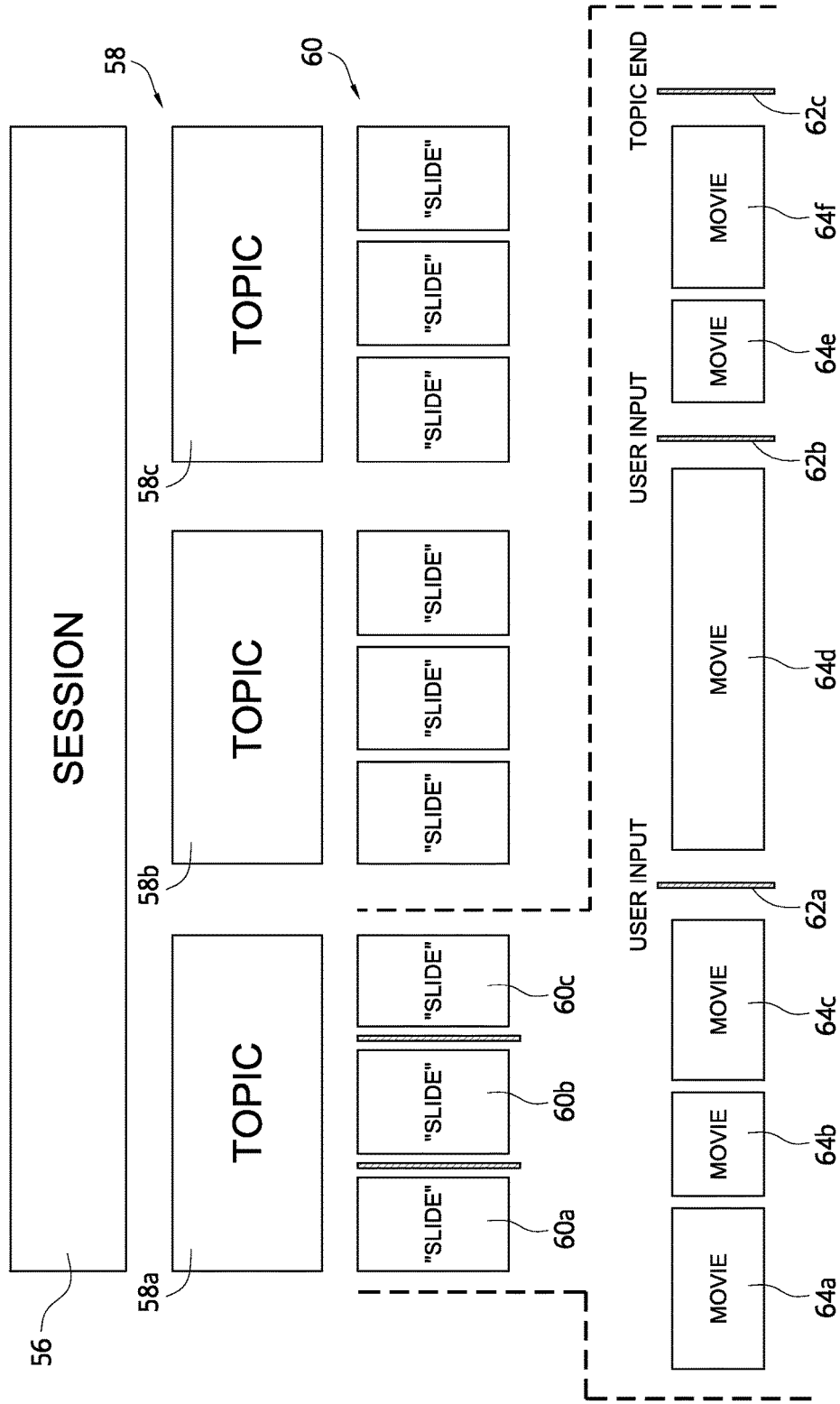
Figure 18:
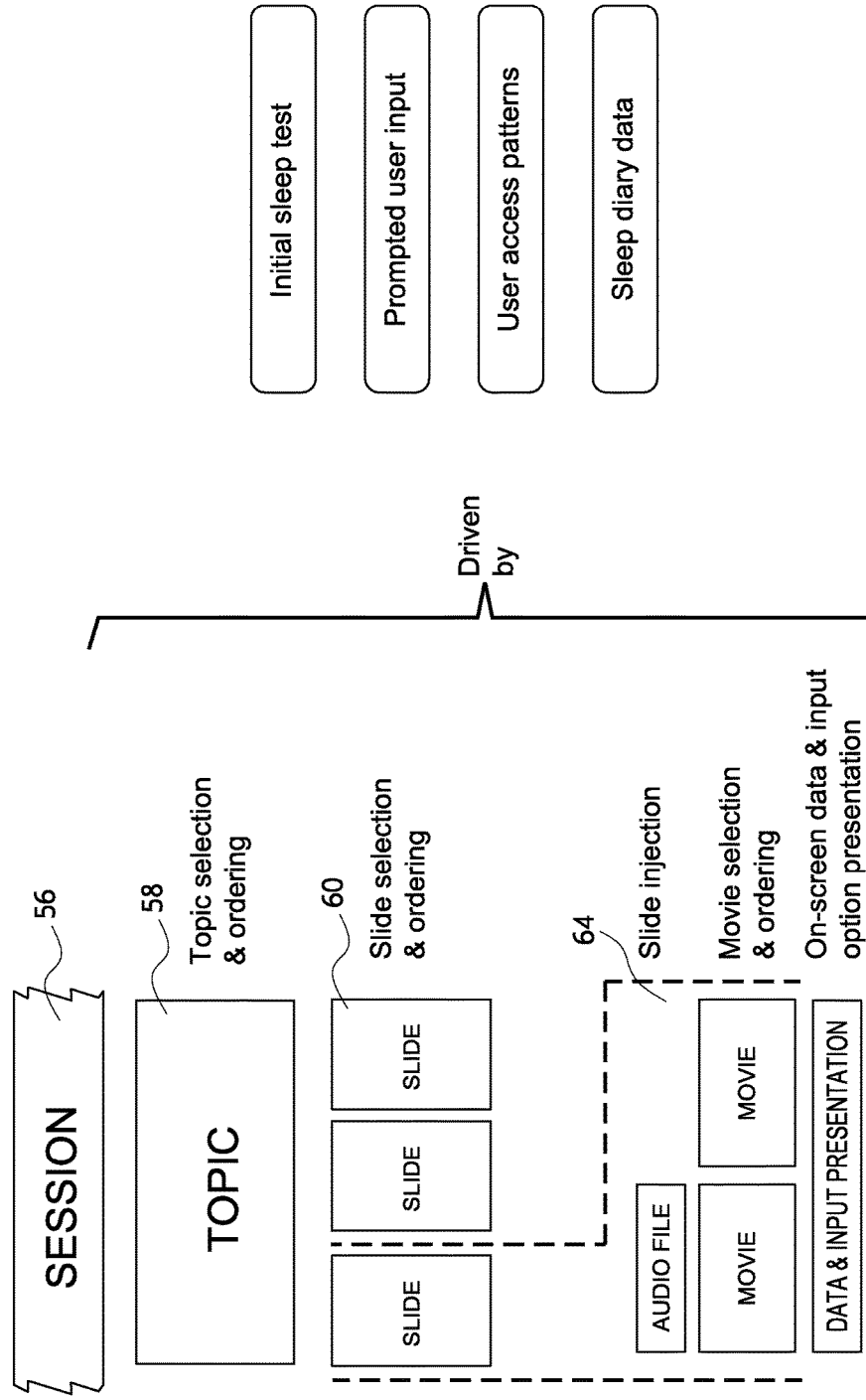

With reference to FIGS. 11 and 12, if desired, a Thought Checker 34 provides a graphical user interface designed to help the user develop a framework to facilitate evaluation of the user's thoughts. In particular, the Thought Checker 34 provides a mechanism for input of bothersome thoughts and applying learning techniques to dealing with the bothersome thoughts. In particular, the Thought Checker 34 includes four fill in boxes. The first box 48 is used by the user to input the thought which is at issue and a second box 50 is provided in which the user is encouraged to input how the thought at issue makes him feel. A third box 52 is provided for the user to input a revised more accurate version of the thought at issue and a fourth box 54 is provided for the user to input how the revised more accurate version of the thought makes him/her feel. These thoughts are saved in the Case File database 18 of the present sleep improvement system 10 so that as the thought reoccurs the user may refer to his or her prior analysis for reinforcement as to the best way in which to handle the thought.

The Planner tool 36 (FIG. 12) provides a graphical user interface designed to help the user develop a framework to facilitate "putting the day to rest". With this in mind, the Planner tool 36 allows the user is physical write down the various thoughts that might bother them in the evening as they try to go to sleep. For example, the Planner tool 36 offers the user the opportunity to write down the good and bad things that happened today, as well as the things that must be done in the future. In conjunction with the things that must be done, the user is provided the opportunity to write down when these things will be completed.

The Relaxation Audio 38 (FIG. 13) provides digital audio designed to allow the user to select MP3 audio to guide relaxation techniques discussed below in detail.

The Reminder tool (in the form of a computer application that provides users with emails/SMS regarding the program and their interactions therewith) 42 assists the user in managing and receiving email and SMS reminders of daily tasks and motivational messages.

Finally, the Community tool 44 (FIG. 15) provides a graphical user interface designed to offer users a peer support network. In particular, each user has a 'helper level' based on how many people have rated their comments as helpful; this allows new users to see which users are to be trusted, and this also acts as an intrinsic reward to the helpful user, as well as creating a supportive atmosphere.

Referring now to FIGS. 16-19, each session 56, regardless of the tools employed, includes specific elements predesigned to effectuate improved sleeping habits. For example, and considering a generic session 56, three topics 58*a-c* are scheduled. Each of the topics 58 includes multiple slides 60. For the point of view of the user interacting with the system via the user interface, a seamless presentation of video material and interactive topics is viewed. However, and considering the various levels of the present system, the user is only aware of the session 56 and topic 58 levels being presented by the sleep improvement system 10. As briefly discussed above, each session 56 is composed of topics 58 and each topic 58 is composed of various slides 60. Each of the slides is composed of video material, for example, short movies or interactive screens, as well as on-screen data overlays, user input interface elements and simultaneous audio files, which are pieced together based upon the information gathered from the user to create material specifically directed to the user.

For example, the first topic 58*a* might be composed of first, second and third slides 60*a*, 60*b*, 60*c* with interactive input sessions 62*a*, 62*b*, wherein the first slide 60*a* is composed of first, second and third movies 64*a*, 64*b*, 64*c* with an interactive user input session 62*a* thereafter, the second slide 60*b* is composed of a fourth movie 64*d* with an interactive user input 62*b* thereafter, and the third slide 60*c* includes fifth and sixth movies 64*e*, 64*f* with a topic ending session 62*c* thereafter.

More particularly, topics 58, slides 60, interactive input sessions 62 and movies/audio 64 of the various sessions 56 are driven by the data inputted by the user during the initial sleep test and initial gathering session, prompted data input by the user during the specific session in progress, the pattern of system access by the user, including the number of times the user has visited that content, the number of times the user has viewed a specific topic, and the progress being made by the user with regard to his or her sleep habits based on their Sleep Diary data. As such, the specific content of any session is varied substantially for any user based upon the specifics of his or her situation.

Figure 19:
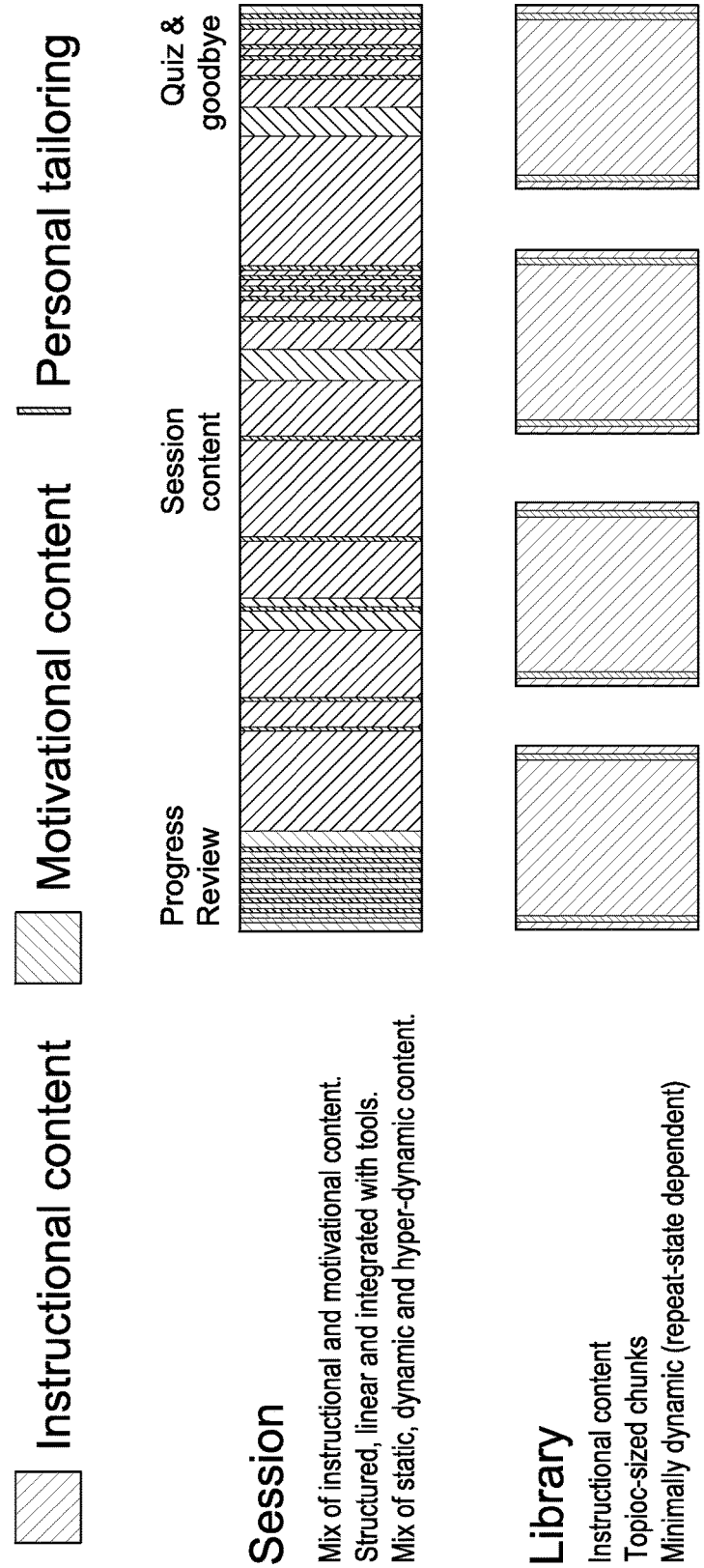

As shown in FIG. 19, the content of pure instructional media is mixed with motivational content and personal tailoring based upon an underlying algorithm that continuous monitors the progress and input of the user.

As discussed above, the sessions in which a user participates are highly customized to the specifics of the individual user. There are six main methods by which the session coordinator 20 personalizes the user experience using the data sources described above:

1. Session Content Selection and Ordering

During a weekly session, the session coordinator 20 displays or does not display sections of content (that is, slides and topics as discussed above) depending on whether that section is relevant to the user (e.g. information on nicotine will not be shown if the user doesn't smoke), or one of a number of variations of a particular section may be selected to be displayed to the user.

Other sections may be presented in a particular order, to ensure that the user receives the most relevant content first (e.g. cognitive techniques which are particularly relevant to the type of negative thoughts that a user experiences most often will be presented first). This is done in a way that maintains the impression of a single seamless movie to the user.

The session coordinator 20 of the present sleep improvement system decides which content to show/not show and the order of content based on an analysis of the user's initial sleep test information (e.g. prominence of various types of negative thought inferred from the user's answers to the initial sleep test) and/or prompted user input (e.g. selection of which bedroom factors are most relevant).

2. Session Content Adaptation

Each section of session content can be adapted by the session coordinator 20 to be particularly relevant to that user. This can involve:

Presenting data about the user's prompted choices, sleep status, thoughts and lifestyle on screen (e.g. which goals they have chosen and how many others have also selected that goal, their current Sleep Efficiency)

Changing the tone and content of the Prof's responses to such user data (e.g. congratulate the user on having made progress towards on high Sleep Efficiency), prompted user inputs (e.g. commiserate if incorrect answers are given to a quiz), or to static properties of each user (e.g. greeting the user by name), all with the purpose of engaging and motivating the user.

Adjusting the information presented on a given topic (e.g. how diet should be approached if the user is overweight).

The present sleep improvement system determines whether to apply these content adaptations to any given section of content depending on properties of each user inferred from their initial sleep test (e.g. whether they are overweight), their recent Sleep Diary data (e.g. whether they have low, medium or high Sleep Efficiency, and whether it is rising or falling), and prompted user input (e.g. correct/incorrect answers to quiz questions).

3. Tool Presentation and Population

During each weekly session a series of online tools are 'unlocked' (i.e. made available to the user) and subsequently populated with data by The Prof as the user progresses through the course. This occurs in the following manner:

1. The Prof introduces and explains a content topic with techniques or exercises for the user to try;
2. The Prof unlocks and presents an online tool that the user can use to help them put this technique or task into practice;
3. The Prof conducts an automated tutorial on how to use the tool, actively manipulating the tool in real time, and then sometimes allowing the user to try it out themselves.
4. The Prof may populate this tool with default data based on the user's initial sleep test and Sleep Diary data.

5. In future session topics, The Prof may add additional information into previously-unlocked tools, based on user input (e.g. adding new actions to the To Do list, adjusting and enriching blocks of time on the user's Schedule) and in real time.

The tools any given user has access to is dictated by the session content they have viewed, which in turn is based on the content selection/ordering process described above. The data inserted into any tool is based on the session content they have viewed, their initial sleep test data, their Sleep Diary data, and prompted user input during each session.

4. Library Article and Community Discussion Unlocking

As the user progresses through the program, expert articles and community discussions relating to the content topics they see are unlocked.

5. Peer Support Matchmaking

At different points in the program The Prof directs the user towards particularly relevant community discussions in an automated fashion. In addition, users early in the program are automatically introduced to 'graduate greeters' (i.e. users who have completed the program and have shown themselves to be positive members of the online community). This matchmaking serves to provide each user with relevant peer support as they progress through the program.

6. Personalized Email and SMS Communication

Between sessions The Prof will send each user personalized emails and/or SMS messages to encourage adherence to the program and provide motivational support. The content and timing of these messages is based on the user's adherence to the program, their personal information (e.g. name), whether they have completed their Sleep Diary on any particular day, the session content they have seen, the time they last accessed the system, their Sleep Diary data and contact preferences.

Throughout the program, the core personalization methods described above are combined to create the final, highly personalized user experience. Here are some examples to illustrate how:

Example 1

Dynamic Role Play

In one section of a weekly session the user engages in the following exercise for the purpose of learning how to evaluate their negative thoughts:
1. The user is asked by The Prof to listen to an animated character express worries about their sleep. Unbeknownst to the user, the character relays an exaggerated version of the user's own worries, attributions, goals, sleep problem type, and how poor sleep affects them during the day, based on their initial sleep test data and chosen personal goals. This is presented seamlessly to the user, yet involves a selection of short movies from a large possible pool being chained together in quick succession.
2. The user is then asked by The Prof to give the character some advice, chosen from a selection of options presented on screen and related to previous information relayed earlier in the session.
3. Once the user has chosen which advice to give the character, The Prof relays this advice verbally to the character, before the character expresses more worries.
4. Once this process has been repeated three times The Prof reveals to the user that the user has in fact been listening to (and giving advice to counteract) versions of their own worries, problems and goals.
5. The user is then asked to consider the advice they have chosen, and to rate how this makes them feel against their personal emotional goals.
6. The Prof then responds to this user input, with the response varying according to whether the user's emotional ratings are higher, lower or mixed when compared to their last recorded emotional goal state. Within this response, The Prof offers relevant, tailored motivational support and explains the principle of thought evaluation that they have just experienced.

Example 2

Weekly Progress Review

At the start of each Session The Prof conducts a review of the user's performance across the past week, including progress towards their personal goals and changes in their sleep pattern and quality. In light of this, The Prof provides motivational support and relevant information to help the user progress further.

The progress review includes the following components:
1. If there are any daily sleep diaries missing from the preceding week, then The Prof asks whether the user has the missing diary information written down. The user then has the chance to enter or edit the stored Sleep Diary data.
2. Depending on the total number of sleep diaries that have been completed after this step, The Prof may fill in any missing diaries with an average from the completed diaries or ask the user to provide an estimate of their sleep over the whole of the previous week.
3. In addition, depending on how many sleep diaries have been completed, and how this number compares to previous weeks' progress reviews, The Prof offers motivation, advice and extra information. This will differ according to the persistence, direction and speed of change in the user's level of adherence.
4. The user answers questions on how they are coping in general, their current emotional state and the level of daytime functioning with reference to their personal goals.
5. The Prof assesses the user's progress against their personal goals based on this prompted user input, their initial sleep test, their Sleep Diary data for the past week, their Sleep Diary data for preceding weeks, and the user's responses during previous progress reviews.
6. The Prof provides an assessment of the user's sleep pattern (expressed as 'Sleep Efficiency', i.e. the proportion of time in bed the user spends asleep) based on their Sleep Diary data from the past week. Depending on the user's current position in the course, their average Sleep Efficiency across the past week, their baseline Sleep Efficiency from their initial sleep test, their Sleep Efficiency at the preceding progress review, the differences between these figures and whether (and at what point) the user has reached certain threshold Sleep Efficiency values, The Prof provides an assessment of the user's progress in improving their sleep pattern and offers associated motivational support.
7. Depending on whether the user's Sleep Efficiency has reached a certain threshold, The Prof may offer the user the opportunity to extend their sleep window on their Schedule. This threshold will be dependent on how far through the course the user has progressed, the user's baseline Sleep Efficiency from their initial sleep test, the change in Sleep Efficiency since then based on the Sleep Diary data, and how the user has said they are coping in general.

8. The Prof gives an overall assessment of the user's progress to date based on a combination of their progress towards their personal goals, their current Sleep Efficiency, and the change in the user's Sleep Efficiency—both since the preceding progress review and since their initial sleep test.

Example 3

Late Night System Access

A user's Schedule tool is set with the time they are usually in bed, or their sleep window depending on the point in the course they have reached. Based on this, the system knows when the user should be in bed. If the user accesses the system during this time window on their mobile phone, they are greeted by The Prof in his dressing gown, who expresses concern about them being awake at this time, and presents them with advice as to what they should do at that moment, including their personal relaxation plan (created by the user with the guidance of The Prof during a previous weekly session) and relaxation audio that they can listen to help them achieve sleep.

The following morning, the user will receive an SMS and/or email message from The Prof an hour after their average rising time, commiserating with the user for being awake the previous night and reminding them to complete their Sleep Diary. The content of any such reminder message will be different if the user does not access the system late at night.

As discussed above, and in accordance with a preferred embodiment, the present computer-based sleep improvement system 10 is designed to employ 6 sessions resulting in a user exhibiting improved sleep habits. More particularly, and as will be discussed below in greater detail with reference to a discussion of a typical multi-session program under which a user is treated, Session One focuses upon "Getting started" with the present computer-based sleep improvement system 10. Session One may include topics such as What causes poor sleep?;
The Sleepio® solution;
Setting your goals;
The commitment we need;
Sleep Efficiency; and
Your Sleep Diary.

Once the initial set-up of Session One is complete the user moves onto Session Two which focuses upon "Your lifestyle, Your bedroom and Your thoughts." Session Two may include topics such as Your lifestyle;
Your bedroom;
The truth about sleep;

Upon the complete of Session Two, the user moves on to Session Three which focuses upon "Your daily schedule" and may include such topics as The Pro-Sleep Schedule;
Before bed: Your Wind Down Routine;
In bed: Your Bed-Sleep Connection;
Reconnecting your bed with sleep;
Sleep Restriction; and
Your new sleep window.

Session Four may focus upon "Your racing mind" and may include topics such as

Analysis of your racing mind;
Cognitive techniques for dealing with the racing mind.

Session Five focuses upon additional cognitive techniques for dealing with the racing mind.

Session Six is "Graduation day" and provides the user with a Summary of the course and Graduation. Finally, Session Seven, that is, "Onwards Maintenance" provides the user with an iterating, personalized progress review and Help topics.

The following presents an exemplary use situation with screen shots of the sleep improvement system 10 as the user progresses through the course of treatment. It should, however, be appreciated, the specific content of the present sleep improvement system 10 is dictated by the information input by the user and the user's interaction with the present system. As such, the specific experience of each user using the present sleep improvement system 10 will vary substantially.

In use, and in accordance with a preferred embodiment of the present invention, a user first registers to use the sleep improvement system 10 and then begins the program.

Once the user is registered, the user will complete an in-depth sleep test. The sleep test takes approximately 10 minutes but provides the present sleep improvement system 10 all the information needed to initially tailor the present sleep improvement system 10 to the specific user. The sleep improvement system 10 utilizes a computerized instructor, which for the purposes of disclosure is referred to herein as The Prof. The Prof functions as the user's personal sleep expert. Once a week, the user visits the Prof for a tailored 20 minute on-line session where the Prof provides the user that week's personalized sleep improvement techniques and leads the user through interactive features specifically focused upon the needs of the specific user. These personalized sleep improvement techniques are based in cognitive behavioral therapy, or CBT, and are clinically proven to be effective in helping most long term poor sleepers improve their sleep.

Between these online sessions, the user, each morning, records how much he or she slept the night before, using the Sleep Diary 24 as discussed above. This process takes less than one minute and the user can complete it online via a mobile device or just simply by writing the information down on paper. The Prof, that is, in the present sleep improvement system 10, uses the Sleep Diary 24 information to report on the user's progress at the start of each session. After each session, new tools are unlocked in the user's personal Case File 66. In particular, and by viewing the Case File 66 using the graphically user interface, the user may see how he or she is progressing against established personal goals. The user can access a wide variety of easy to use on-line tools to help put the new techniques into practice. These range from a Daily Schedule 30 with automatic reminders to a Thought Checker 34 tool, if desired, to help the user deal with a racing mind.

The sleep improvement system 10 also provides a Library 32 of important information that the user may read to gain valuable information on a variety of topics. The underlying team of experts behind the present sleep improvement system 10 has written over 100 expert articles on every topic in the present sleep improvement system 10. As such, if the user wants to know the science behind a certain technique, or have a more detailed question, then the Library 32 is the appropriate resource.

Finally, the present sleep improvement system 10 includes a Community tool 44. Using the Community tool 44 the user can meet other people currently taking part in the present sleep improvement system 10 and learn from 'program graduates', in other words users who have already been through the program. In addition once a week users can take part in a live group session with a sleep expert from the present sleep improvement system 10 who will answer that week's most popular question.

Once the user is properly logged in, the user is presented with a screen welcoming the user to the present sleep improvement system 10. The user is presented with a sleep test that takes 5-10 minutes and provides the user with everything needed to tailor the present sleep improvement system 10 for the specific user. Upon indicating a desire to proceed, the user is presented with an in-depth sleep test composed of nine pages. In this report, the user is asked a series of questions:

the country in which he or she lives,
the postal/zip code,
the year the user was born and
whether the user is male or female.

In addition, the user is asked to explain whether he or she has a partner and whether he or she has children that live with them. The user's employment status is requested. In addition, the user is asked whether he or she is a shift worker,
the general self-rated status of the user's physical health and
the general self-rated status of the user's mental health.

The user is then asked
whether he/she ever smokes tobacco and how often,
whether he/she drinks alcohol and how often,
whether he/she consumes caffeine and how often,
whether he/she exercises and how often,
whether he/she considers themselves to be overweight,
whether he/she takes sleeping pills prescribed by a doctor, and
whether he/she takes any non-prescription sleep remedies.

The user is then asked
what time they normally go to bed,
what time they normally turn out the lights,
how long it takes them to fall asleep,
how many times during the night they wake on average,
how long are they awake in total during the night due to these wakings,
what time do they normally wake for the final time in the morning,
what time do they normally get out of bed, and
on a typical day, how long do they nap for in total.

The user is then asked to explain whether any of these conditions have existed over the past months and how disruptive they have been to their sleep, in particular, they are asked about
bodily discomfort,
noise,
an uncomfortable bed,
room temperature,
light levels,
children and
their partner.

The user is then asked to rate their sleep quality overall and to explain the extent that sleep has troubled them in general. The user is also asked how many nights do they have problems with their sleep and how long have they have had a problem with their sleep. Further, the user is asked how likely is it in the past month that they would fall asleep during the day time without intending to or that they would struggle to stay awake while they were doing things. The user is then asked what the problem seems to be when they don't have a good night's sleep. For example, whether they can't get into a comfortable position in bed,
whether they can't get their sleep pattern into a proper routine;
whether they find it hard to let go and relax their body;
whether they try too hard to sleep;
whether they don't feel tired enough at bedtime; and
whether they worry that they won't cope tomorrow if they don't sleep well.

The user is then asked to what extent poor sleep has affected various aspects of their life, for example,
their energy;
their relationships;
their ability to stay awake during the day;
their concentration;
their ability to get through work;
their mood;
their behavior; and
their ability to look after other people.

Next, the user is asked to explain how poor sleep has made them feel over the past month, for example, helpless; frustrated; negative; worried; alone. The user is also asked to explain whether when they lie awake in bed they think about
what happened today and what they've got on tomorrow,
how out of control their sleep is and not knowing what to do about it,
their body feeling hot or cold,
a pounding in their head,
things that have happened in the past and how they worked out,
how long they have been lying awake,
noises they can hear in the house or outside,
what the future might hold and how they should be doing things to work out well,
how they're going to cope tomorrow if they don't sleep well tonight, and
trivial things of no importance that go through my mind.

With this information the sleep test is complete providing the present sleep improvement system 10 with a major source of information to personalize the present sleep improvement system 10 for the user's particular needs. This data is stored in a Case File database 18 of the present sleep improvement system 10.

With the background information for the stored in the Case File database 18, the user is instructed to click "Visit the Prof" when they are ready to start the program associated with the present sleep improvement system 10. On clicking "Visit the Prof", a graphical user interface is presented and then the user is asked what they would like to do, for example, start the session or hear more explanation about various topics that might be of interest to the user. Where the user desires to learn more about something, the user may return to previous viewed topics from previous sessions. When the user desires to start the session, he or she simply clicks upon the "Start Session" button and the user is presented with an introductory video featuring The Prof. Thereafter, a summary of the upcoming Session One is provided. Session One may include topics including
What causes persistent sleep problems;
An explanation of the sleeping solution offered by the present system;
Setting personal goals;
The commitment needed to achieve goals of the present system;

An explanation of Sleep Efficiency;

In introduction to the Sleep Diary 24 tool; and

A weekly quiz.

A summary of the first section of the Session is then provided and the user is asked if they would like this section to be repeated or whether they would like to continue with the process (such regular requests to repeat the prior section are provided by the present sleep improvement system 10 throughout the course of the sleep treatment procedure of the present invention). The Prof then explains ways in which the present sleep improvement system 10 will help to achieve the goals of good sleep. A summary of Sessions One through Six is then provided. The sleep improvement system 10 then summarizes how a user goes about setting his or her goals. The Prof then explains the best way to proceed in establishing goals. The overall goal might be getting to sleep more easily, staying asleep during the night, getting a better quality of sleep, sleeping longer each night, or having a more reliable sleep schedule.

The user is then interactively engaged with regard to the concept of the desired goals associated with using the present sleep improvement system 10. In particular, the user is prompted to choose one overall goal. The Prof then asks for information about what the user wishes to improve with regard to their daily life as it is affected by sleep and the user is prompted to select which of these best applies. Thereafter, the Prof prompts the user to explain, emotionally, how they would like to feel after using the system. The Prof then provides a summary of the user's goals and asks for confirmation as to whether the user is happy with the specified goals. The sleep improvement system 10 then creates a Case File 66 which is presented to the user on the graphical user interface. These goals show the user's progress and the tools that have been provided to the user so as use in conjunction with the present sleep improvement system 10.

The user is then presented with a Commitment designed to establish a relationship between the sleep improvement system 10 and the user. The user is then requested to execute an agreement. The confirmation of the Commitment is then presented to the user.

The next section, Sleep Efficiency, is presented. An explanation of sleep efficiency is provided wherein it is explained to the user that sleep efficiency relates to the ratio of one's time asleep to one's time in bed. The Prof then summarizes the user's personal sleep efficiency providing an interface demonstrating the information. Thereafter, sleep efficiency information is incorporated into the user's Case File 66 and the user is asked to continue.

The sleep improvement system 10 then explains the Sleep Diary 24 of the present sleep improvement system 10. The user is then asked to maintain and input requested information on a daily basis using the Sleep Diary 24 for the purpose of creating diary of the user's sleeping patterns. The Sleep Diary 24 is completed each and every morning, by providing the specific information requested. The user is then presented with an updated To-Do List 28 specifying the user must fill in the Sleep Diary 24 every day.

The user is then presented with a weekly quiz. The quiz asks the user various questions regarding the prior lesson. The sleep improvement system 10, after the quiz, than presents a wrap up of the first session and provides tasks for the upcoming week. The user is then prompted to book a reminder for the next session. As a follow up to Session One, the user is sent an email summary of the prior week's activity. The user is similarly provided with an account summary from which he or she may view information available in the Sleep Diary 24, the Case File 66, the Library 32 or the Community tool 44.

After completing the Session One the user proceeds to fill in the Sleep Diary 24 for the following seven days. After the Sleep Diary 24 has been filled in, for seven days, the user logs in and begins Session Two. Session Two is initiated with a summary of the prior week's sleeping with a view towards the Sleep Diary 24. At this point, the user is asked a series of questions about the effect the present sleep improvement system 10 is having upon their well-being. For example, the user is asked to provide an overall rating for the past week, the user is asked how sleeping has affected their mood and their ability to get through the week. The sleep improvement system 10 further asks the user to what extent poor sleep has made the user feel frustrated and negative, that is, questions that relate directly to the user's specific personal goals. The questions are utilized to calculate the user's progress, and the Sleep Diary 24 and Case File 66 are accordingly updated.

During Session Two, The Prof explains issues relating to the user's lifestyle and sleep. Amongst these issues are discussions relating to peoples belief that they can't change their habits, and stressful life events and their relation to your sleep patterns. Session Two continues with discussions relating to the combination and relationship between caffeine and sleep, nicotine and sleep, alcohol and sleep, diet and sleep, and exercise and sleep. During these sections interactive questioning is incorporated into the process. For example, the user is asked to identify which foods are thought to contain caffeine.

Session Two continues with teachings regarding progressive relaxation. The sleep improvement system 10 offers Relaxation Audio tools to assist the user in applying relaxation techniques. In addition, Session Two explains autogenic training, how relaxation works to help poor sleep, the use of relaxation techniques, progressive relaxation, and general relaxation. Session Two also goes into explaining the relationship between sleeping pills and sleep quality. With this complete, the user is offered ideas for use in making lifestyle changes and the Case File 66 is accordingly updated. Once the user makes the appropriate selections, the Daily Schedule 30 of the Case File 66 is updated so as to identify the lifestyle changes the user intends upon making.

Session Two then continues with a discussion of bedroom items using interactive cues. For example, the graphical user interface of the Session Two offers the user a screen showing items commonly found in a bedroom and asks the user to identify various items the user believes are sleep-unfriendly. As the user does this, the sleep improvement system 10 explains the ideal light level and the importance of a sleeping environment, finding the right bedding and mattress, and the importance of the sleeping environment. This section also discusses the effects of noise and how a user may deal with noise as well as temperature and how a user may get the right temperature for sleep. With a complete understanding as to bedroom elements that might having a bearing on one's ability to sleep, the user is offered things to try in making bedroom changes and the Case File 66 is accordingly updated. Once the user makes the appropriate selections the To Do List 28 of the Case File 66 is updated so as to identify the bedroom changes the user intends upon making.

Finally, truths regarding sleep are explained, for example, that sleep problems normally pass quite quickly, that feelings of irritability are not always due to bad sleep, that people need less sleep later in life, that the average adult sleeps 7-8 hours a night (true), that we do not tend to sleep better later in the night, and that you should not try to make up for lost sleep on subsequent nights.

The user is then presented with a weekly quiz. The quiz asks the user various questions regarding the prior lesson. The sleep improvement system 10, after the quiz, then presents a wrap up of the first session and provides tasks for the upcoming week. The user is then prompted to book a reminder for the next session. As a follow up to Session Two, the user is sent an email summary of the prior week's activity. The user is similarly provided with an account summary from which he or she may view information available in the Sleep Diary 24, the Case File 66, the Library 32 or the Community tool 44.

After completing Session Two, the user goes back to filling in the Sleep Diary 24 and then returns for the completion of Session Three. As with Session Two, Session Three begins with a summary of the prior week's sleeping with a view towards the Sleep Diary 24. At this point, the user is again asked a series of questions about the effect the present sleep improvement system 10 is having upon their wellbeing. For example, the user is asked to provide an overall rating for the past week, the user is asked how sleeping has affected their mood and their ability to get through the week. The sleep improvement system 10 further asks the user to what extent poor sleep has made the user feel frustrated and negative. The questions are utilized to calculate the user's progress, and the Case File 66 is accordingly updated.

Once this preliminary work is completed, Session Three continues with lessons regarding the pro-sleep schedule, the user's wind down routine, the bed-sleep connection, reconnecting the user's bed with sleep, sleep restrictions, sleep schedules and the weekly quiz.

Considering first the pro-sleep schedule, the sleep improvement system 10 provides an explanation of how the user feels during the day and how to deal with such feelings. For example, does the user feel sleepy during the day and what should the user be doing during the day to promote healthy sleep.

The Prof then explains an appropriate wind down routine for preparing for bedtime. The sleep improvement system 10 interactively explains that users should focus on passive relaxation as bedtime approaches for the purpose of facilitating letting go and heading off to sleep. This is accomplished by asking the user to answer questions regarding whether certain activities are active, physical, passive and mental. The sleep improvement system 10 then offers the user various options (wind down activities and pre-bed tasks) they might wish to incorporate into their wind down routine and updates the Case File 66 with the selected wind down activities. For example, the user is asked to choose between listening to music, watching TV, going for a stroll or looking at photographs. The user is also asked to choose amongst various nightly pre-bed tasks including locking up the house, getting into nightwear, brushing teeth and feeding the pet. After the user has made these choices, the Daily Schedule 30 and To Do List 28 of the Case File 66 are updated accordingly.

Further, the bed-sleep connection is explained. In conjunction with this connection, explanations are provided regarding how the user can improve their bed/sleep connection;
the science behind the bed/sleep connection:
the 'quarter of an hour rule';
when the user should return to bed in the event he or she wakes up during the middle of the night; and
why you should do nothing but sleep in your bedroom.

In conjunction with the likelihood that a user will be waking up in the middle of the night, the user is interactively asked to choose which wake up activities will be used during this woken period as a mechanism to help the user fall back asleep quickly and efficiently. The user is also interactively asked to choose the location at which he or she will relax during these woken periods. The user's selections are added to the To Do List 28 and Daily Schedule 30 of the Case File 66.

Finally, sleep restriction is discussed. If appropriate a new restricted 'sleep window' is suggested for the user, which the user can position in their Daily Schedule. Common concerns about Sleep Restriction are then discussed. As with the other interactive elements of the present sleep improvement system 10, the user's Daily Schedule 30 of the Case File 66 is updated with this information.

The user is then presented with a weekly quiz. The quiz asks the user various questions regarding the prior lesson. The sleep improvement system 10, after the quiz, then presents a wrap up of Session Three and provides tasks for the upcoming week. The user is then prompted to book a reminder for the next session. As a follow up to Session Three, the user is sent an email summary of the prior week's activity. The user is similarly provided with an account summary from which he or she may view information available in the Sleep Diary 24, the Case File 66, the Library 32 or the Community tool 44.

As the user progresses and continues using the sleep improvement system 10 for an additional week, the time for Session Four is reached. As with Sessions Two and Three, Session Four begins with a summary of the prior week's sleep based on the contents of the Sleep Diary 24. At this point, the user is again asked a series of questions about the effect the present sleep improvement system 10 is having upon their wellbeing. For example, the user is asked to provide an overall rating for the past week, the user is asked how sleeping has affected their mood and their ability to get through the week. The sleep improvement system 10 further asks the user to what extent poor sleep has made the user feel frustrated and negative. The questions are utilized to calculate the user's progress, and the Case File 66 is accordingly updated. Finally, the user may be offered the chance to update their 'sleep window'. It is appreciated based upon the foregoing disclosure that the decision of The Prof to extend the user's sleep window is based upon a complicated series of conditions which dictate whether a user is offered the chance to extend their sleep window.

During Session Four the user is taught about different types of negative thought that prevent sleep. The user is then taught three techniques for dealing with these thoughts, which, depending on which types of thoughts are the greatest problem to the user may be leaving the thoughts behind, challenging the thoughts and focusing away from the thoughts. The three techniques and their order, as taught to the user, are dictated by which types of thoughts are the greatest problems to the user.

With regard to the idea of leaving thoughts behind, the user is provided with a Planner tool 36 in the Case File 66. The Planner tool 36 allows the user is physical write down the various thoughts that might bother them in the evening as they try to go to sleep. For example, the Planner tool 36 offers the user the opportunity to write down the good and bad things that happened today, as well as the things that must be done in the future. In conjunction with the things that must be done, the user is provided the opportunity to write down when these things will be completed. As with other tools, the Daily Schedule 30 and To Do List 28 of the Case File 66 are updated to remind the user of his or her need to utilize the Planner tool 36 on a daily basis.

This session continues with a discussion regarding the ability of users to challenge their thoughts and provides cognitive techniques in depth. In conjunction with this technique for dealing with a racing mind, the user is provided with an additional tool, that is, the Thought Checker 34 tool. The Prof further explains using the Thought Checker 34 to challenge the thoughts. In particular, and as discussed above, the Thought Checker 34 provides a mechanism for input of bothersome thoughts and applying leaning techniques to dealing with the bothersome thoughts. In particular, the Thought Checker 34 includes four fill in boxes. The first box 48 is used by the user to input the thought which is at issue and a second box 50 is provided in which the user is encouraged to input how the thought at issue makes him feel. A third box 52 is provided for the user to input a revised more accurate version of the thought at issue and a fourth box 54 is provided for the user to input how the revised more accurate version of the thought makes him/her feel. These thoughts are saved in the Case File database 18 of the present sleep improvement system 10 so that as the thought reoccurs the user may refer to his or her prior analysis for reinforcement as to the best way in which to handle the thought.

The user is finally taught techniques for focusing away thoughts using autogenic training and imagery. In conjunction with these techniques, the user is provided with audio tools; for example, an imagery audio and an autogenic training audio.

The user is then presented with a weekly quiz. The quiz asks the user various questions regarding the prior lesson. The sleep improvement system 10, after the quiz, then presents a summary of the previous session and provides tasks for the upcoming week. The user is then prompted to book a reminder for the next session. As a follow up to Session Four, the user is sent an email summary of the session content and the tasks for the week ahead. The user is similarly provided with a summary from which he or she may view information available in the Sleep Diary 24, the Case File 66, the library 32 or the Community tool 44.

After completing Session Four, the user completes his or her Sleep Diary 24 for another week while working on the various techniques taught in Sessions One, Two, Three and Four, and proceeds with Session Five. As with Session Two, Three and Four, Session Five begins with a summary of the prior week's sleeping with a view towards the Sleep Diary 24. At this point, the user is again asked a series of questions about the effect the present sleep improvement system 10 is having upon their wellbeing. For example, the user is asked to provide an overall rating for the past week, the user is asked how sleeping has affected their mood and their ability to get through the week. The sleep improvement system 10 further asks the user to what extent poor sleep has made the user feel frustrated and negative. The questions are utilized to calculate the user's progress, and the Case File 66 is accordingly updated. Finally, and as with FIG. 4, the user may be offered the chance to update their 'sleep window'. As discussed above, it is appreciated based upon the foregoing disclosure that the decision of The Prof to extend the user's sleep window is based upon a complicated series of conditions which dictate whether a user is offered the chance to extend their sleep window.

In Session Five the user is provided with more techniques to deal with their negative thoughts, which may be thought blocking, accepting (mindfulness) and embracing (paradoxical thinking) thoughts, depending on the type of thoughts that bother the user most. It should be appreciated the techniques and order in which they are taught in Sessions Four and Five will vary depending upon the specific needs of the user.

The To Do List 28 of the Case File 66 is then updated with this information reminding the user of the various mechanisms for dealing with undesired thoughts. The user is then presented with a weekly quiz. The quiz asks the user various questions regarding the prior lesson. The sleep improvement system 10, after the quiz, then presents a summary of the previous session and details the user's tasks for the upcoming week. The user is then prompted to book a reminder for the next session. As a follow up to Session Five, the user is sent an email summary of the session content, their progress and the tasks for the coming week. The user is similarly provided with an account summary from which he or she may view information available in the Sleep Diary 24, the Case File 66, the Library 32 or the Community tool 44.

Finally Session Six is reached and a summary of the course is presented to the user in conjunction with a graduation ceremony. Session Seven onwards is an iterating session, where the progress review changes depending on progress of user, and they have a chance to extend their sleep window if they meet certain criteria.

While the preferred embodiments have been shown and described, it will be understood that there is no intent to limit the invention by such disclosure, but rather, is intended to cover modifications and alternate constructions falling within the spirit and scope of the invention.

What is claimed is:

1. A computer-based sleep improvement system applying system intelligence to up-to-date user-reported data for assisting a user in the proactive improvement of sleep and treatment of insomnia, comprising:
a central server maintaining a library of information related to treatment of insomnia, the central server including:
a video database of session video material;
an audio database of session audio material;
an updatable case file database of information regarding the user and sleep habits of the user, the case file database includes a data source employed to personalize the sessions to each user, the data source being composed of an initial sleep test, sleep diary data, user access patterns, and prompted user input; and
a plurality of tools assisting the user in treating insomnia, wherein the plurality of tools include at least one of a Sleep Diary, a To Do List, a Daily Schedule, a Library, a Thought Checker, a Planner tool, a Compare Sleep Tags tool, Relaxation Audio(s), a Recommended reading tool, Stats, a Sleep Report, Reminders, a Community tool, or a combination thereof;
a session coordinator, in the form of a microprocessor, creating sessions of customized presentations for the user based upon the library of information, each session is composed of a plurality of topics which are in turn composed of various slides, wherein each of the various slides is composed of video material, on-screen data overlays, user input interface elements used in gathering information regarding the user and the sleep habits of the user, and audio, which are pieced together based upon information gathered from the user to create individual movie and audio elements appearing to the user as a single seamless interactive movie specifically directed to the user; and
a graphical user interface linked to the central server, the graphical user interface providing access to the single seamless interactive movie, video material, technical literature, and the plurality of tools.

2. The computer-based sleep improvement system according to claim 1, wherein the session coordinator decides upon content for the sessions based on an analysis of the user's initial sleep test information and prompted user input.

3. The computer-based sleep improvement system according to claim 2, wherein the sessions are weekly interactive video-based customized presentation, delivered over the Internet, during which the user learns cognitive and behavioral techniques.

4. The computer-based sleep improvement system according to claim 1, wherein the graphical user interface is accessed via a computer connected to a global communication network.

5. The computer-based sleep improvement system according to claim 1, wherein the session coordinator includes functionality for providing email, SMS communications and/or social networking.

6. The computer-based sleep improvement system according to claim 1, wherein the session coordinator includes a program interface, application program interface, and/or web applications.

7. The computer-based sleep improvement system according to claim 1, wherein the Sleep Diary provides a user interface for recording a sleep pattern, a quality rating and lifestyle factors.

8. The computer-based sleep improvement system according to claim 1, wherein the Sleep Report provides a representation of Sleep Test data of the user.

9. The computer-based sleep improvement system according to claim 8, wherein the Compare Sleep Tags tool allows the user to compare sleep on nights associated with any particular "tag" added in the Sleep Diary.

10. The computer-based sleep improvement system according to claim 1, wherein the Relaxation Audio provides digital audio designed to allow the user to select MP3 audio to guide relaxation techniques.

11. The computer-based sleep improvement system according to claim 1, wherein the Reminder tool assists the user in managing and receiving email and SMS reminders of tasks and motivational messages.

12. The computer-based sleep improvement system according to claim 1, wherein the Community tool provides a graphical user interface offering the user a peer support network.

* * * * *